United States Patent
Salvestro et al.

(10) Patent No.: US 11,033,191 B2
(45) Date of Patent: *Jun. 15, 2021

(54) MEDICAL DEVICE INCLUDING MANIPULABLE PORTION WITH CONNECTED ELONGATE MEMBERS

(71) Applicant: Kardium Inc., Burnaby (CA)

(72) Inventors: Aldo Antonio Salvestro, Burnaby (CA); John Andrew Funk, Delta (CA); Kelly Wilson Watkinson, Burnaby (CA); Saar Moisa, Vancouver (CA)

(73) Assignee: KARDIUM INC., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/900,150

(22) Filed: Jun. 12, 2020

(65) Prior Publication Data

US 2020/0305726 A1    Oct. 1, 2020

Related U.S. Application Data

(63) Continuation of application No. 16/258,996, filed on Jan. 28, 2019, now Pat. No. 10,716,477, which is a (Continued)

(51) Int. Cl.
*A61B 18/18* (2006.01)
*A61B 5/04* (2006.01)
(Continued)

(52) U.S. Cl.
CPC ............... *A61B 5/01* (2013.01); *A61B 5/287* (2021.01); *A61B 5/6858* (2013.01);
(Continued)

(58) Field of Classification Search
CPC ...... A61B 18/1492; A61B 2018/00267; A61B 2018/00214; A61B 2018/0022;
(Continued)

(56) References Cited

U.S. PATENT DOCUMENTS

| 4,643,186 A | 2/1987 | Rosen |
| 5,309,910 A | 5/1994 | Edwards |

(Continued)

FOREIGN PATENT DOCUMENTS

| WO | 2012100184 A2 | 7/2012 |
| WO | 2012100185 A2 | 7/2012 |

OTHER PUBLICATIONS

International Search Report issued in Intl. Appln. No. PCT/CA2015/051078 dated Feb. 9, 2016.

(Continued)

*Primary Examiner* — Joseph A Stoklosa
*Assistant Examiner* — Brian M Antiskay
(74) *Attorney, Agent, or Firm* — Rossi, Kimms & McDowell LLP

(57) ABSTRACT

A medical system may include a shaft member and a structure physically coupled to the shaft member. A portion of the shaft member may be sized to be delivered through a bodily opening leading to a bodily cavity. The structure may include at least two flexible couplings, each flexible coupling extending transversely from an intermediate portion of a respective one of at least two elongate members of the structure. The flexible coupling extending transversely from the intermediate portion of a first one of the at least two elongate members forms at least a part of a first closed loop arranged to receive a portion of the flexible coupling of a second one of the at least two elongate members therethrough to limit a spacing between the intermediate portions of the first and the second ones of the at least two elongate members.

21 Claims, 11 Drawing Sheets

Related U.S. Application Data continuation of application No. 15/978,609, filed on May 14, 2018, now Pat. No. 10,278,590, which is a continuation of application No. 14/579,234, filed on Dec. 22, 2014, now Pat. No. 9,993,160.

(60) Provisional application No. 61/924,525, filed on Jan. 7, 2014.

(51) Int. Cl.

| | | |
|---|---|---|
| A61B 5/01 | (2006.01) | |
| A61B 18/14 | (2006.01) | |
| A61N 1/05 | (2006.01) | |
| A61B 5/00 | (2006.01) | |
| A61B 5/287 | (2021.01) | |
| A61B 18/00 | (2006.01) | |

(52) U.S. Cl.
CPC .......... *A61B 18/1492* (2013.01); *A61N 1/056* (2013.01); *A61B 5/6853* (2013.01); *A61B 5/6859* (2013.01); *A61B 2018/00267* (2013.01); *A61B 2018/00357* (2013.01); *A61B 2018/00577* (2013.01); *A61B 2018/00791* (2013.01); *A61B 2018/00875* (2013.01)

(58) Field of Classification Search
CPC .......... A61B 5/0422; A61B 2018/1467; A61B 2018/1475; A61B 2018/1435; A61B 5/6858; A61B 2018/00285; A61B 5/6852; A61B 5/6853; A61M 25/0147; A61M 2205/0266; A61M 25/0152; A61M 25/10; A61M 25/0043
USPC ........ 600/372–375, 380–381, 393, 508–509; 606/32–52; 607/122
See application file for complete search history.

(56) References Cited

U.S. PATENT DOCUMENTS

| | | | |
|---|---|---|---|
| 5,345,936 A | 9/1994 | Pomeranz | |
| 5,351,679 A | 10/1994 | Mayzels | |
| 5,456,254 A | 10/1995 | Pietroski | |
| 5,575,810 A | 11/1996 | Swanson | |
| 5,830,210 A | 11/1998 | Rudko | |
| 5,893,847 A | 4/1999 | Kordis | |
| 6,216,043 B1 * | 4/2001 | Swanson | A61B 5/0422 600/374 |
| 9,101,342 B2 | 8/2015 | Saleh | |
| 9,492,228 B2 | 11/2016 | Lopes | |
| 2002/0026187 A1 | 2/2002 | Swanson | |
| 2004/0181139 A1 | 9/2004 | Falwell | |
| 2008/0183036 A1 | 7/2008 | Saadat | |
| 2009/0131930 A1 | 5/2009 | Gelbart | |
| 2009/0171274 A1 | 7/2009 | Harlev | |
| 2011/0213231 A1 | 9/2011 | Hall | |
| 2013/0041314 A1 | 2/2013 | Dillon | |
| 2013/0172883 A1 | 7/2013 | Lopes | |
| 2014/0114307 A1 | 4/2014 | Moisa | |
| 2014/0257069 A1 | 9/2014 | Eliason | |
| 2015/0057519 A1 | 2/2015 | Ben-David | |
| 2017/0224958 A1 | 8/2017 | Cummings | |

OTHER PUBLICATIONS

Written Opinion issued in Intl. Appln. No. PCT/CA2015/051078 dated Feb. 9, 2016.
Extended European Search Report issued in European Application No. 15854296.9 dated Oct. 18, 2017.
Office Action issued in U.S. Appl. No. 14/579,234 dated Oct. 5, 2017.
Notice of Allowance issued in U.S. Appl. No. 14/579,234 dated Feb. 20, 2018.
Office Action issued in U.S. Appl. No. 15/978,609 dated Nov. 1, 2018.
Office Action issued in copending U.S. Appl. No. 15/498,951 dated Sep. 18, 2020.
Response filed in U.S. Appl. No. 16/258,996 dated Dec. 3, 2019.
Response filed in U.S. Appl. No. 16/258,996 dated Dec. 23, 2019.
Notice of Allowance issued in U.S. Appl. No. 16/258,996 dated Mar. 13, 2020.
Response filed in U.S. Appl. No. 16/258,996 dated Sep. 8, 2019.
Office Action issued in U.S. Appl. No. 16/258,996 dated Oct. 4, 2019.
Preliminary Remarks filed in U.S. Appl. No. 16/258,996 dated Jan. 28, 2019.
Non-Final Office Action issued in U.S. Appl. No. 16/258,996 dated Jul. 11, 2019.
Notice of Allowance issued in U.S. Appl. No. 15/978,609 dated Mar. 6, 2019.
Communication under Rule 71(3) EPC, Intention to Grant issued in European Appln. No. 15854296.9 dated Mar. 28, 2019.
Amendment filed in U.S. Appl. No. 14/579,234 dated Dec. 22, 2017.
Amendment filed in U.S. Appl. No. 15/978,609 dated Jan. 18, 2019.
Response filed in copending U.S. Appl. No. 15/498,951 dated Dec. 17, 2020.
Office Action issued in copending U.S. Appl. No. 15/498,951 dated Jan. 26, 2021.
Amendment filed in copending U.S. Appl. No. 15/498,951 dated Mar. 24, 2021.

* cited by examiner

MEDICAL DEVICE INCLUDING MANIPULABLE PORTION WITH CONNECTED ELONGATE MEMBERS

CROSS-REFERENCE TO RELATED APPLICATIONS

This application is a continuation of prior U.S. patent application Ser. No. 16/258,996, filed Jan. 28, 2019, now U.S. Pat. No. 10,716,477, issued Jul. 21, 2020, which is a continuation of prior U.S. patent application Ser. No. 15/978,609, filed May 14, 2018, now U.S. Pat. No. 10,278,590, issued May 7, 2019, which is a continuation of prior U.S. patent application Ser. No. 14/579,234, filed Dec. 22, 2014, now U.S. Pat. No. 9,993,160, issued Jun. 12, 2018, which claims priority benefit of U.S. Provisional Application No. 61/924,525, filed Jan. 7, 2014. The entire disclosure of the applications cited in this paragraph is hereby incorporated herein by reference.

TECHNICAL FIELD

Aspects of this disclosure generally are related to a medical device system including a manipulable portion that includes connected elongate members. In some embodiments, a structure of the manipulable portion includes the elongate members, and the structure is selectively movable between a delivery configuration and an expanded or deployed configuration.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. Accordingly, a need in the art exists for improved intravascular or percutaneously deployed catheter systems.

SUMMARY

At least the above-discussed need is addressed and technical solutions are achieved by various embodiments of the present invention. In some embodiments, a medical system includes a shaft member and a structure. The shaft member may include a portion sized to be delivered through a bodily opening leading to a bodily cavity. The structure may be physically coupled to the shaft member. The structure may include a plurality of elongate members. Each elongate member of the plurality of elongate members may include a proximal end, a distal end, and a respective intermediate portion positioned between the respective proximal end and the respective distal end. The structure may be selectively moveable between a delivery configuration in which the structure is suitably sized to be delivered through the bodily opening to the bodily cavity, and an expanded configuration in which the structure has a size too large to be delivered through the bodily opening to the bodily cavity. The respective intermediate portions of at least two of the plurality of elongate members may be angularly spaced with respect to one another about an axis when the structure is in the expanded configuration. The structure may include at least two flexible couplings. Each flexible coupling may extend transversely (e.g., in a direction having a directional component extending transversely) from the intermediate portion of a respective one of the at least two of the plurality of elongate members. Each location on the intermediate portion from which the flexible coupling extends transversely may be spaced from each of the proximal and distal ends of the respective one of the at least two of the plurality of elongate members. The flexible coupling extending transversely from the intermediate portion of at least a first one of the at least two of the plurality of elongate members may form at least a part of a first closed loop arranged to receive a portion of the flexible coupling of a second one of the at least two of the plurality of elongate members therethrough to limit a spacing between the intermediate portions of the first and the second ones of the at least two of the plurality of elongate members to not exceed a defined amount when the structure is in the expanded configuration.

In some embodiments, the flexible coupling extending transversely from the intermediate portion of the second one of the at least two of the plurality of elongate members forms at least part of a second closed loop. In some embodiments, no portion of the flexible coupling extending transversely from the intermediate portion of the first one of the at least two of the plurality of elongate members is received through the second loop at least when the spacing between the respective locations of the first and the second ones of the at least two of the plurality of elongate members is sized by the defined amount. In some embodiments, no portion of the flexible coupling extending transversely from the intermediate portion of the first one of the at least two of the plurality of elongate members is received through the second loop when the flexible coupling extending transversely from the intermediate portion of the first one of the at least two of the plurality of elongate members is tensioned. In some embodiments, each of the first and the second closed loops extends along a respective continuous closed path, each respective continuous closed path not encircling the other respective continuous closed path. In some embodiments, the continuous closed path of the first closed loop does not pass through the continuous closed path of the second closed loop. In some embodiments, the continuous closed path of the second closed loop does pass through the continuous closed path of the first closed loop.

In some embodiments, at least another part of the first closed loop is formed by at least a part of the intermediate portion of the first one of the at least two of the plurality of elongate members.

In some embodiments, the flexible coupling extending transversely from the intermediate portion of the first one of the at least two of the plurality of elongate members includes a first end portion, a second end portion, and an elongate portion extending between the first end portion and the second end portion, at least one of the first end portion and the second end portion physically coupled to the intermediate portion of the first one of the at least two of the plurality of elongate members. In some embodiments, the intermediate portion of the first one of the at least two of the plurality of elongate members includes a plurality of material layers and each of the at least one of the first end portion and the second end portion is physically coupled to the intermediate portion of the first one of the at least two of the plurality of elongate members at a location between a respective pair of adjacent ones of the plurality of material layers.

In some embodiments, the flexible coupling extending transversely from the intermediate portion of the first one of the at least two of the plurality of elongate members includes a first end portion, a second end portion, and an elongate portion extending between the first end portion and the second end portion, each of the first end portion and the second end portion physically coupled to the intermediate portion of the first one of the at least two of the plurality of elongate members.

In some embodiments, the intermediate portion of at least the second one of the at least two of the plurality of elongate members includes a thickness, a first side, a second side, and an aperture extending across the thickness from the first side to the second side, the first closed loop arranged to extend through the aperture in the intermediate portion of the second one of the at least two of the plurality of elongate members.

In some embodiments, the intermediate portion of at least the second one of the at least two of the plurality of elongate members comprises a thickness, a first side, a second side, and an aperture extending across the thickness from the first side to the second side, and wherein the first closed loop extends along a path from the intermediate portion of the first one of the at least two of the plurality of elongate members through the aperture from the second side to the first side of the intermediate portion of the second one of the at least two of the plurality of elongate members to a location where the portion of the flexible coupling of the second one of the at least two of the plurality of elongate members is arranged to extend through the first closed loop. The second side may face inwardly toward the axis when the structure is in the expanded configuration and the first side may face outwardly away from the axis when the structure is in the expanded configuration.

In some embodiments, the intermediate portion of at least the second one of the at least two of the plurality of elongate members includes a thickness, a first side, a second side, and an aperture extending across the thickness from the first side to the second side, and wherein the first closed loop is arranged to extend through the aperture from the second side to the first side of the intermediate portion of the second one of the at least two of the plurality of elongate members, and wherein the aperture is sized to restrict movement of the first closed loop through the aperture from the first side toward the second side of the intermediate portion of the second one of the at least two of the plurality of elongate members when the portion of the flexible coupling of the second one of the at least two of the plurality of elongate members extends through the first closed loop. In some embodiments, the medical system may include one or more transducers located on the first side of the intermediate portion of the second one of the at least two of the plurality of elongate members.

In some embodiments, the medical system includes one or more transducers located on the structure. In some embodiments, the medical system includes one or more transducers located on each of at least one of the at least two of the plurality of elongate members.

Various systems may include combinations and subsets of all the systems summarized above.

In some embodiments, some or all of any of the systems or devices summarized above or otherwise described herein, or one or more combinations thereof, may be controlled by one or more control methods for executing some or all of the functionality of such systems or devices summarized above or otherwise described herein. In some embodiments, a computer program product may be provided that includes program code portions for performing some or all of any of such control methods, when the computer program product is executed by a computing device. The computer program product may be stored on one or more computer-readable storage mediums. In some embodiments, each of the one or more computer-readable storage mediums is a non-transitory computer-readable storage medium. In some embodiments, such control methods are implemented or executed in part or in whole by at least one data processing device or system upon configuration thereof by one or more programs executable by the at least one data processing device or system and stored in one or more computer-readable storage mediums. In some embodiments, each of the one or more computer-readable storage mediums is a non-transitory computer-readable storage medium.

BRIEF DESCRIPTION OF THE DRAWINGS

It is to be understood that the attached drawings are for purposes of illustrating aspects of various embodiments and may include elements that are not to scale.

FIGS. 5A, 5B, 5C, 5D, 5E, 5F, 5G, 5H-1, and 5H-2 illustrate apparatus for, among other things, connecting the elongate members of a manipulable portion, such as that shown in FIGS. 2, 3A, and 3B, which may limit spacing between elongate members according to example embodiments.

DETAILED DESCRIPTION

Figure 1:
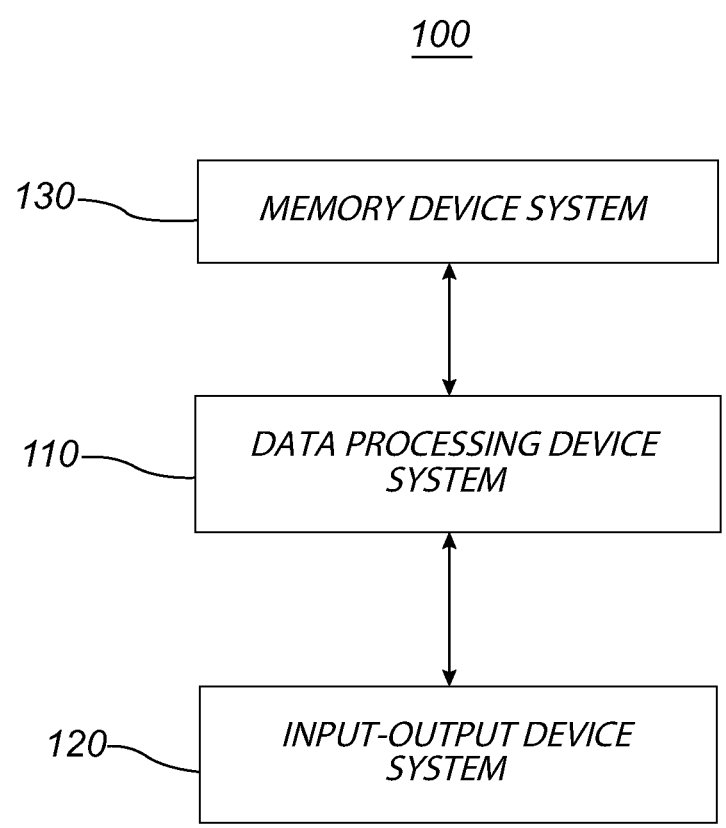
FIG. 1 is a schematic representation of a system according to example embodiments, system including a data processing device system, an input-output device system, and a memory device system.

In the following description, certain specific details are set forth in order to provide a thorough understanding of various embodiments of the invention. However, one skilled in the art will understand that the invention may be practiced without one or more of these details. In some instances, well-known structures have not been shown or described in detail to avoid unnecessarily obscuring descriptions of various embodiments of the invention.

Reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this specification are not necessarily all referring to the same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is used herein merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase 'based at least upon A' includes A as well as the possibility of one or more other additional elements or functions besides A. In the same manner, the phrase, 'based upon A' includes A, as well as the possibility of one or more other additional elements or functions besides A. However, the phrase, 'based only upon A' includes only A. For another similar example, each of the phrases 'configured at least to A' and 'configured to at least A' includes a configuration to perform A, as well as the possibility of one or more other additional actions besides A. In the same manner, the phrase 'configured to A' includes a configuration to perform A, as well as the possibility of one or more other additional actions besides A. However, the phrase 'configured only to A', for example, means a configuration to perform only A.

The word "ablation" as used in this disclosure should be understood to include, for example, any disruption to certain properties of tissue. Most commonly, the disruption is to the electrical conductivity and is achieved by heating, which can be generated with resistive or radio-frequency (RF) techniques for example. However, any other technique for such disruption may be included when the term "ablation" is used, such as mechanical, chemical, or optical techniques.

The word "fluid" as used in this disclosure should be understood to include, for example, any fluid that can be contained within a bodily cavity or can flow into or out of, or both into and out of a bodily cavity via one or more bodily openings positioned in fluid communication with the bodily cavity. In the case of cardiac applications, fluid such as blood flows into and out of various intra-cardiac cavities (e.g., a left atrium or right atrium).

The phrase "bodily opening" as used in this disclosure should be understood to include, for example, a naturally occurring bodily opening or channel or lumen; a bodily opening or channel or lumen or perforation formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The phrase "bodily cavity" as used in this disclosure should be understood to mean a cavity in a body. The bodily cavity may be a cavity provided in a bodily organ (e.g., an intra-cardiac cavity or chamber of a heart). The bodily cavity may be provided by a bodily vessel.

The word "tissue" as used in some embodiments in this disclosure should be understood to include, for example, any surface-forming tissue that is used to form a surface of a body or a surface within a bodily cavity, a surface of an anatomical feature or a surface of a feature associated with a bodily opening positioned in fluid communication with the bodily cavity. The tissue can include, for example, part or all of a tissue wall or membrane that defines a surface of the bodily cavity. In this regard, the tissue can form an interior surface of the cavity that surrounds a fluid within the cavity. In the case of cardiac applications, tissue can include, for example, tissue used to form an interior surface of an intra-cardiac cavity such as a left atrium or right atrium. In some embodiments, tissue is non-excised tissue. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include, for example, an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed.

The term "program" in this disclosure should be interpreted as a set of instructions or modules that can be executed by one or more components in a system, such as a controller system or data processing device system, in order to cause the system to perform one or more operations. The set of instructions or modules can be stored by any kind of memory device, such as those described subsequently with respect to the memory device system 130 shown in FIG. 1. In addition, instructions or modules of a program may be described as being configured to cause the performance of a function or action.

The phrase "configured to" in this context is intended to include, for example, at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions.

The word "device" and the phrase "device system" both are intended to include, for example, one or more physical devices or sub-devices (e.g., pieces of equipment) that interact to perform one or more functions, regardless of whether such devices or sub-devices are located within a same housing or different housings. In this regard, the word "device" may equivalently be referred to as a "device system".

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

FIG. 1 schematically illustrates a system 100, according to some embodiments. The system 100 may be a medical system and may include a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement methods by controlling, driving, or otherwise interacting with various structural components described herein, including, but not limited to, one or more of the various structural components illustrated in FIGS. 2, 3A, 3B, 4, and 5. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute various methods implemented by the data processing device system 110. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single housing or data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include or be a processor-accessible (or computer-readable) data storage medium. In some embodiments, each of the phrases "processor-accessible memory" and "processor-accessible memory device" is intended to include or be a non-transitory processor-accessible (or computer-readable) data storage medium. In some embodiments, the memory device system 130 may be considered to include or be a non-transitory processor-accessible (or computer-readable) data storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, a computer, a processor-accessible memory device, some or all of a catheter device system (e.g., FIGS. 2, 3A, 3B, 4, 5), or any device or combination of devices from which a desired selection, desired information, instructions, or any other data is input to the data processing device system 110. The input-output device system 120 may include a user-activatable control system that is responsive to a user action. The input-output device system 120 may include any suitable interface for receiving a selection, information, instructions, or any other data from other devices or systems described in various ones of the embodiments. In this regard, the input-output device system 120 may include various ones or portions of other systems or devices described in various embodiments.

The input-output device system 120 also may include an image generating device system, a display device system, a processor-accessible memory device, some or all of a catheter device system (e.g., FIGS. 2, 3A, 3B, 4, 5), or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions, or any other data to other devices or systems described in various ones of the embodiments. In this regard, the input-output device system 120 may include various other devices or systems described in various embodiments.

Various embodiments of catheter systems are described herein. It should be noted that any catheter system described herein may also be referred to as a medical system. Some of the described devices of such systems are medical devices that are percutaneously or intravascularly deployed. Some of the described devices are deployed through a bodily opening that is accessible without puncturing, cutting or otherwise perforating bodily tissue to create an access to the bodily opening. Some of the described devices employ transducer-based devices or device systems. Some of the described devices are moveable between a delivery or unexpanded configuration in which a portion of the device is sized, shaped, or both for passage through a bodily opening leading to a bodily cavity, and an expanded or deployed configuration in which the portion of the device has a size, shape, or both too large for passage through the bodily opening leading to the bodily cavity. An example of an expanded or deployed configuration is when the portion of the catheter system is in its intended-deployed-operational state inside the bodily cavity. Another example of the expanded or deployed configuration is when the portion of the catheter system is being changed from the delivery configuration to the intended-deployed-operational state to a point where the portion of the device now has a size, shape, or both too large for passage through the bodily opening leading to the bodily cavity.

Figure 2:
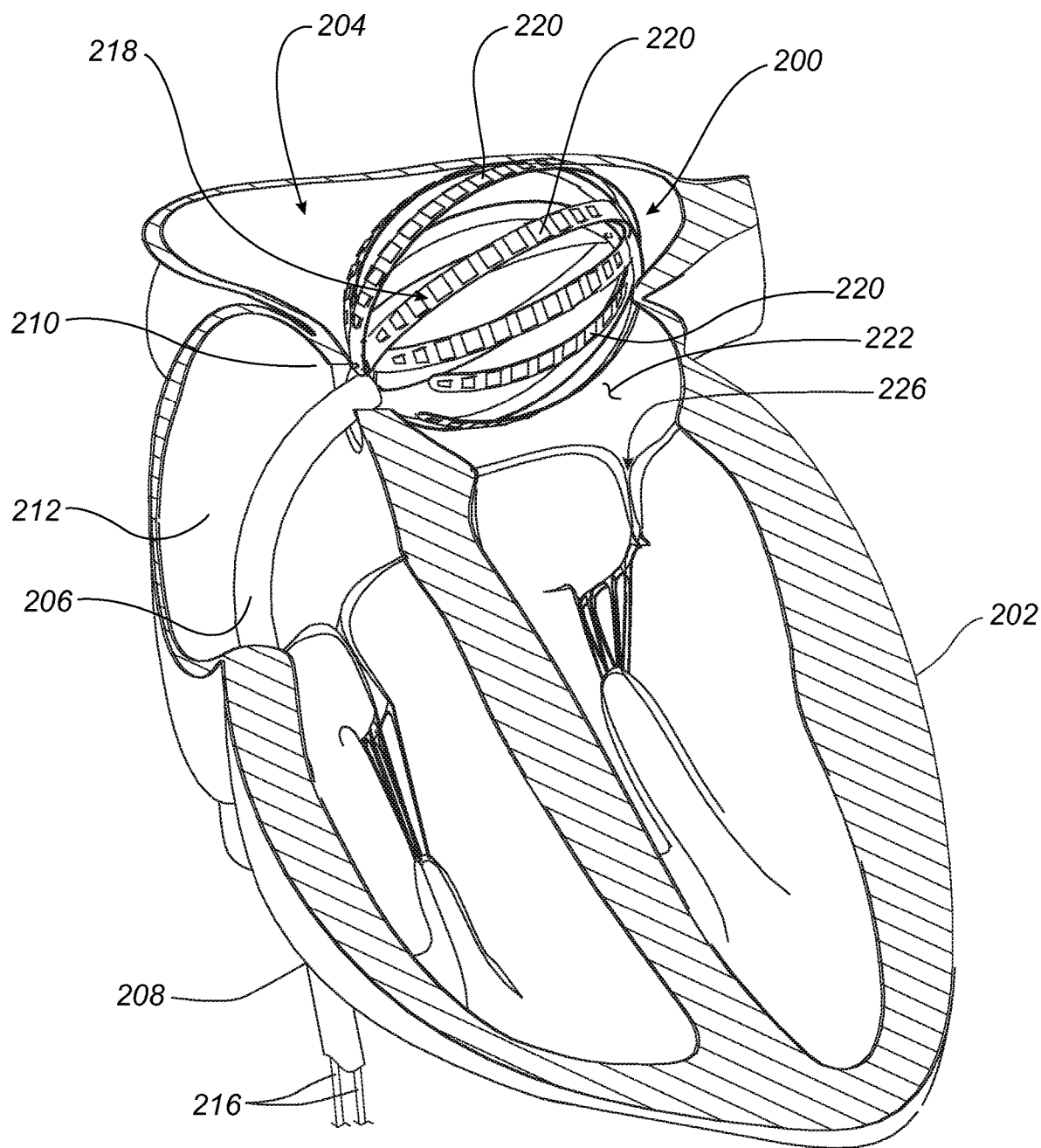
FIG. 2 is a cutaway diagram of a heart showing a manipulable portion percutaneously placed in a left atrium of a heart according to example embodiments.

In some example embodiments, the catheter system includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical device system to map the cavity, for example using positions of openings or ports into and out of the cavity to determine a position or orientation (i.e., pose), or both of the portion of the device in the bodily cavity. In some example embodiments, the described devices are capable of ablating tissue in a desired pattern within the bodily cavity. In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing. FIG. 2 shows a medical system, according to some embodiments, which may be a portion of a catheter system, according to some embodiments, such portion including a transducer-based device 200, which may be at least part of a medical device useful in investigating or treating a bodily organ, for example a heart 202, according to some example embodiments. The transducer-based device 200 may also be referred to as a manipulable portion, due to its ability to have its size, shape, or both size and shape altered, according to some embodiments described below. Transducer-based device 200 can be percutaneously or intravascularly inserted into a portion of the heart 202, such as an intra-cardiac cavity like left atrium 204.

In the example of FIG. 2, the illustrated portion of the catheter system also includes a catheter 206, which may be inserted via the inferior vena cava 208 and may penetrate through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens. The lumen(s) may carry one or more communications or power paths, or both. For example, the lumens(s) may carry one or more electrical conductors 216 (two shown in this embodiment). Electrical conductors 216 provide electrical connections to transducer-based device 200 that are accessible externally from a patient in which the transducer-based device 200 is inserted.

In various embodiments, transducer-based device, or manipulable portion, 200 includes a frame or structure 218, which assumes an unexpanded configuration for delivery to left atrium 204. Structure 218 is expanded (i.e., shown in a deployed or expanded configuration in FIG. 2) upon delivery to left atrium 204 to position a plurality of transducers 220 (three called out in FIG. 2) proximate the interior surface formed by tissue 222 of left atrium 204. In this regard, it can be stated that one or more of the transducers 220 are moveable with one or more parts of the transducer-based device, or manipulable portion, 200. In some embodiments, at least some of the transducers 220 are used to sense a physical characteristic of a fluid (i.e., blood) or tissue 222, or both, that may be used to determine a position or orientation (i.e., pose), or both, of a portion of transducer-based device 200 within, or with respect to left atrium 204. For example, transducers 220 may be used to determine a location of pulmonary vein ostia (not shown) or a mitral valve 226, or both. In some embodiments, at least some of the transducers 220 may be used to selectively ablate portions of the tissue 222. For example, some of the transducers 220 may be used to ablate a pattern or path around various ones of the bodily openings, ports or pulmonary vein ostia, for instance to reduce or eliminate the occurrence of atrial fibrillation.

Figure 3A:
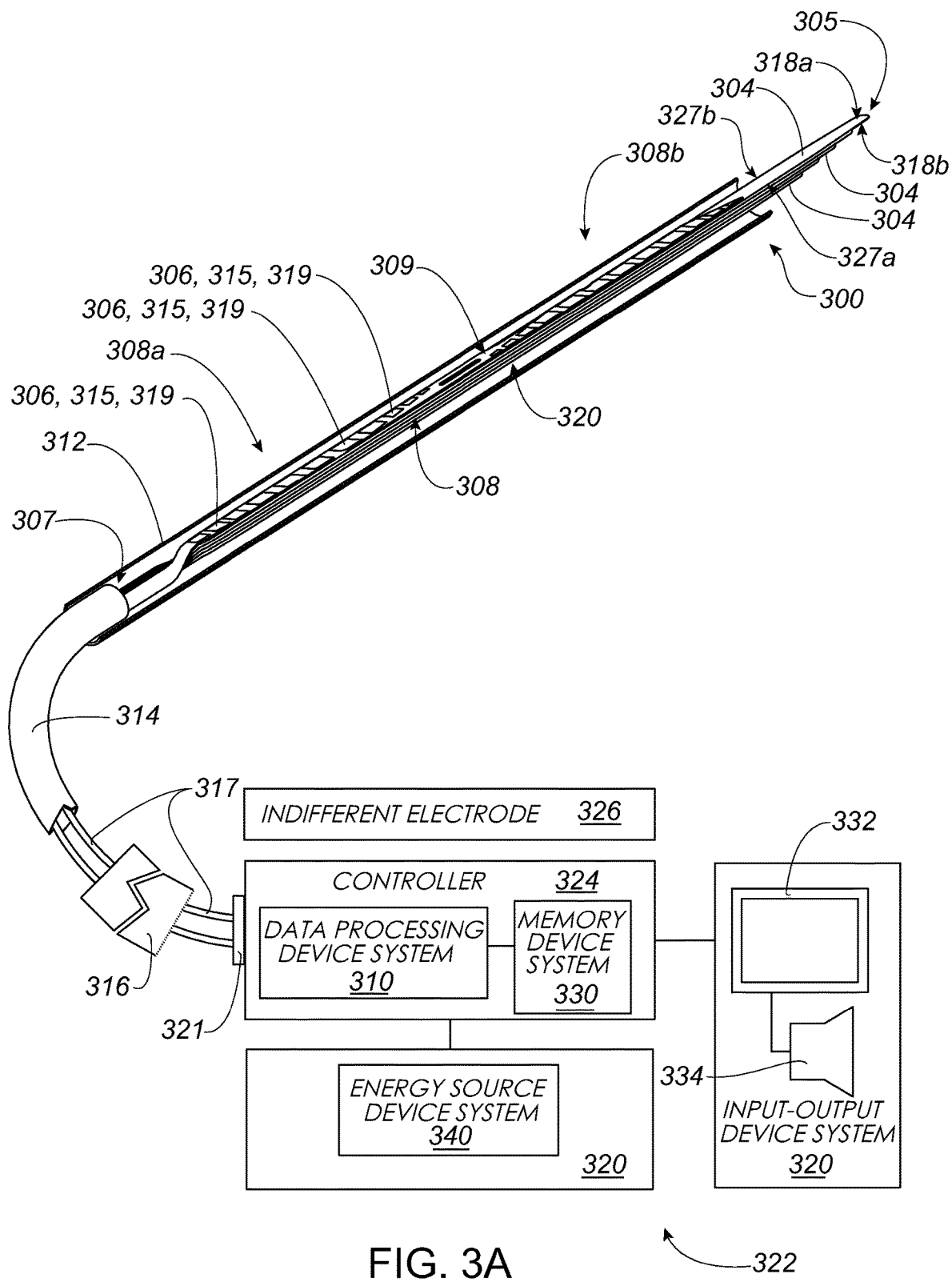
FIG. 3A is a partially schematic representation of a medical device system according to example embodiments, the medical device system including a data processing device system, an input-output device system, a memory device system, and a manipulable portion having a plurality of transducers and an expandable structure shown in a delivery or unexpanded configuration.
Figure 3B:
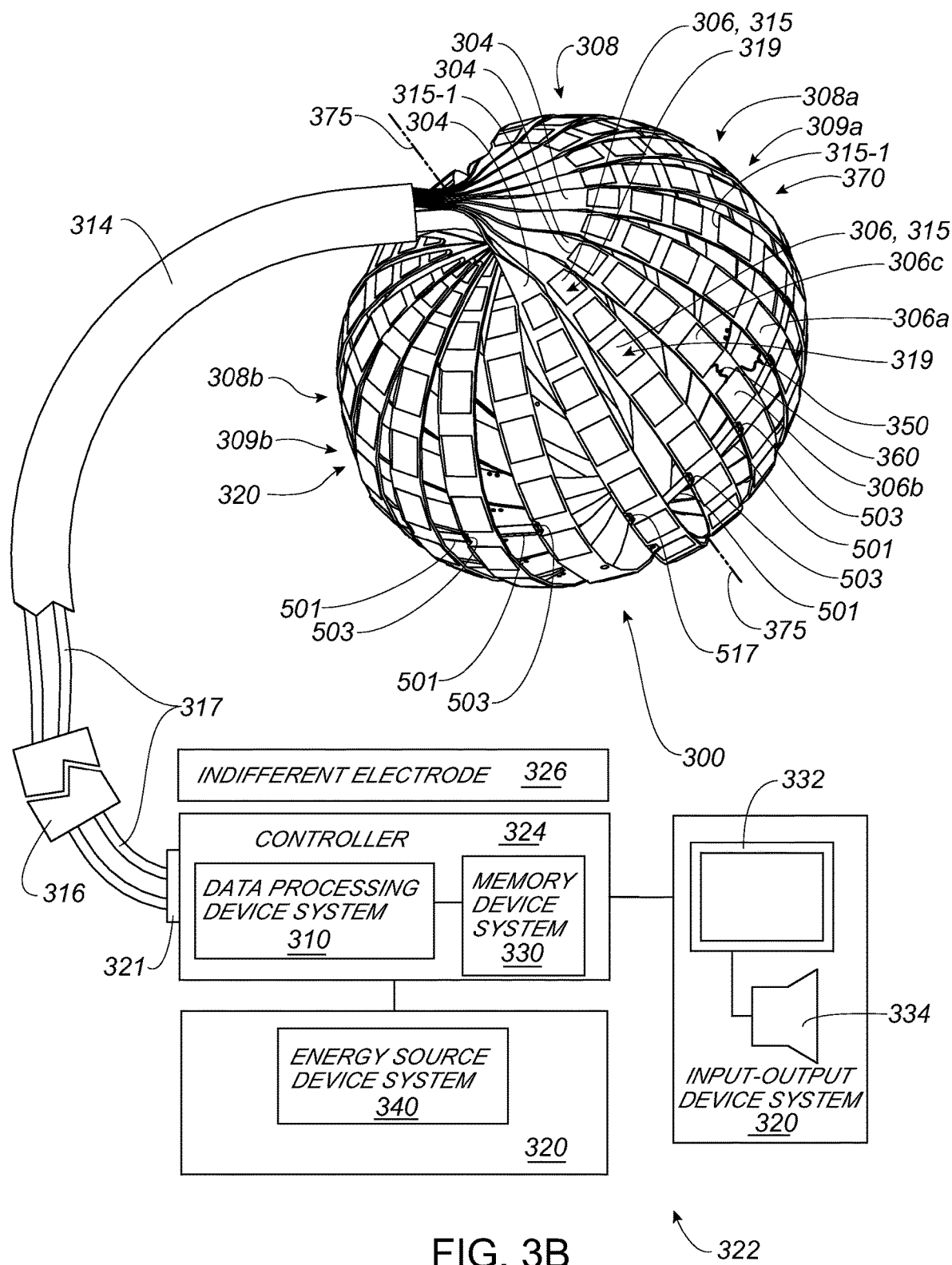
FIG. 3B is the medical device system of FIG. 3A with the expandable structure shown in a deployed or expanded configuration, according to example embodiments.

FIGS. 3A and 3B show a medical system, according to some embodiments, which may include a catheter system (i.e., a portion thereof shown schematically) that includes a transducer-based device 300 according to some embodiments. The transducer-based device 300 may correspond to the transducer-based device 200 and, in this regard, may also be referred to as a manipulable portion, due to its ability to have its size, shape, or both size and shape altered, according to some embodiments described below. Transducer-based device 300 may include a plurality of elongate members 304 (three called out in each of FIGS. 3A and 3B) and a plurality of transducers 306 (only some called out in each of FIGS. 3A and 3B, and some are indicated with a lowercase letter after the reference numeral 306). As will become apparent, the plurality of transducers 306 are positionable within a bodily cavity. For example, in some embodiments, the transducers 306 are able to be positioned in a bodily cavity by movement into, within, or into and within the bodily cavity, with or without a change in a particular configuration of the plurality of transducers 306. In some embodiments, the plurality of transducers 306 are arrangeable to form a two- or three-dimensional distribution, grid or array of the transducers capable of mapping, ablating, or stimulating an inside surface of a bodily cavity or lumen without requiring mechanical scanning. As shown, for example, in FIG. 3A, the plurality of transducers 306 are arranged in a distribution receivable in a bodily cavity, as the transducer-based device 300 and its plurality of transducers 306 are located within the catheter sheath 312. Stated differently, in FIG. 3A, for example, the plurality of transducers 306 are arranged in a distribution suitable for delivery to a bodily cavity. (It should also be noted, however, that the expanded or deployed configuration (e.g., FIGS. 2, 3B) may also be considered to have the transducers 306 arranged in a distribution receivable in a bodily cavity, as the transducer-based device 300 and its transducers 306 may be returned to the delivery configuration of FIG. 3A, for example.) In some embodiments, each of the transducers 306 includes an electrode 315 having an energy transmission surface 319 suitable for transmitting energy in various directions. (Some of the electrodes 315 are illustrated with a lowercase letter following the reference numeral 315. Similarly, some of the energy transmission surfaces 319 are illustrated with a lowercase letter following the reference numeral 319.) In some embodiments, tissue-ablating energy is transmitted toward or away from an electrode 315. In some embodiments, tissue-based electrophysiological energy is transmitted toward an electrode 315.

The elongate members 304 form part of a manipulable portion, and in various embodiments, are arranged in a frame or structure 308 that is selectively moveable between an unexpanded or delivery configuration (e.g., as shown in FIG. 3A) and an expanded or deployed configuration (e.g., as shown in FIG. 3B) that may be used to position portions of various ones of the elongate members 304 against a tissue surface within the bodily cavity or position portions of various ones of the elongate members 304 in the vicinity of or in contact with the tissue surface. In this regard, it may also be stated that the transducer-based device, or manipulable portion, 300 is selectively moveable between an unexpanded or delivery configuration (e.g., as shown in FIG. 3A) and an expanded or deployed configuration (e.g., as shown in FIG. 3B). In some embodiments, the transducer-based device, or manipulable portion, 300, (e.g., the structure 308 thereof) has a size, shape, or both a size and a shape in the unexpanded or delivery configuration suitable for percutaneous delivery through a bodily opening (for example, via catheter sheath 312, not shown in FIG. 3B) to the bodily cavity. In some embodiments, structure 308 has a size, shape, or both a size and a shape in the expanded or deployed configuration too large for percutaneous delivery through a bodily opening (i.e., via catheter sheath 312) to the bodily cavity. The elongate members 304 may form part of a flexible circuit structure (i.e., also known as a flexible printed circuit board (PCB) circuit). The elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern. The number of elongate members 304 depicted in FIG. 3B is non-limiting.

Figure 4:
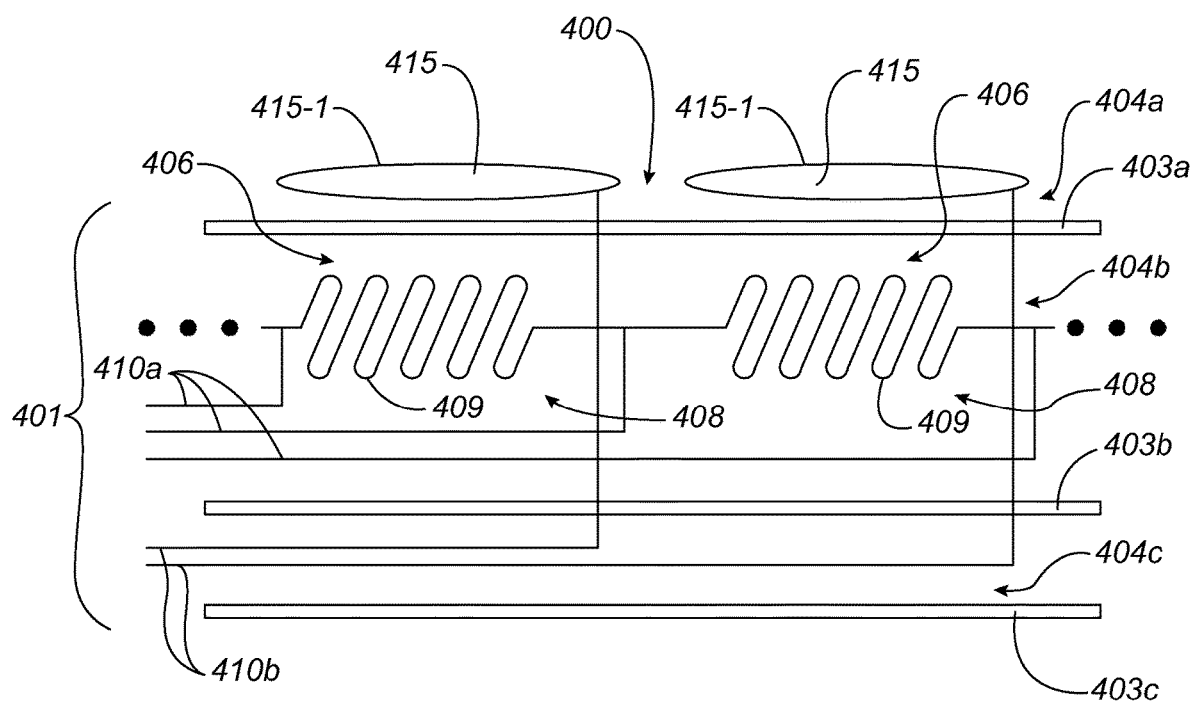
FIG. 4 is a schematic representation of a transducer-based device that includes a flexible circuit structure according to example embodiments.

FIG. 4 is a schematic side elevation view of at least a portion of a transducer-based device 400 that includes a flexible circuit structure 401 that is employed to provide a plurality of transducers 406 (two called out) (which may correspond to transducers 306) according to some embodiments. The transducer-based device 400 may be all or a portion of a medical device, according to some embodiments. In some embodiments, the flexible circuit structure 401 may form part of a structure (e.g., structure 308) that is selectively moveable between a delivery configuration sized for percutaneous delivery and an expanded or deployed configuration sized too large for percutaneous delivery. In some embodiments, the flexible circuit structure 401 may be located on, or form at least part of, of a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (i.e., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 (which may correspond to electrodes 315) have respective electrode edges 415-1 that form a periphery of an electrically conductive surface associated with the respective electrode 415. FIG. 3B shows another example of electrode edges 315-1 and illustrates that the electrode edges can define electrically-conductive-surface-peripheries of various shapes.

Returning to FIG. 4, electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example.

Energy that is sufficient for tissue ablation may be dependent upon factors including tissue characteristics, transducer location, size, shape, relationship with respect to another transducer or a bodily cavity, material or lack thereof between transducers, et cetera.

In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form at least part of a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive member 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow). In some embodiments in which the transducer-based device is deployed in a bodily cavity (e.g., when the transducer-based device 300 is part of a catheter system and may be arranged to be percutaneously or intravascularly delivered to a bodily cavity via a catheter), it may be desirable to perform various mapping procedures in the bodily cavity. For example, when the bodily cavity is an intra-cardiac cavity, a desired mapping procedure can include mapping electrophysiological activity in the intra-cardiac cavity. Other desired mapping procedures can include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as the left atrium.

Referring to FIGS. 3A, 3B, transducer-based device or manipulable portion 300 may communicate with, receive power from, or be controlled by a control system 322. In some embodiments, elongate members 304 can form a portion of an elongated cable 316 of control leads 317, for example by stacking multiple layers, and terminating at a connector 321 or other interface with control system 322. The control leads 317 may correspond to the electrical connectors 216 in FIG. 2 in some embodiments. The control system 322 may include a controller 324 that may include a data processing device system 310 (e.g., data processing device system 110 from FIG. 1) and a memory device system 330 (e.g., memory device system 130 from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

In some embodiments, the controller 324 may be configured to control deployment, expansion, retraction, or other manipulations of the shape, positioning, or both shape and positioning of the transducer-based device (e.g., manipulable portion) 300 at least by driving (e.g., by an electric or other motor) movement of various actuators or other catheter system components.

In this regard, in some embodiments, some of which are described later in this disclosure, the controller 324 is at least part of a control system, which may include one or more actuators, configured to advance at least part of the transducer-based device (e.g., 200, 300, or 400), at least a portion of which may be considered a manipulable portion, out of the catheter sheath 312, retract at least part of the transducer-based device back into the catheter sheath 312, expand, contract, or otherwise change at least part of the shape of the transducer-based device.

Control system 322 may include an input-output device system 320 (e.g., an example of 120 from FIG. 1) communicatively connected to the data processing device system 310 (i.e., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a health care provider or technician. For example, output from a mapping process may be displayed on a display device system 332.

Control system 322 may also include an energy source device system 340 including one or more energy source devices connected to transducers 306. In this regard, although FIG. 3A shows a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 may be fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include various electrical current sources or electrical power sources as energy source devices. In some embodiments, an indifferent electrode 326 is provided to receive at least a portion of the energy transmitted by at least some of the transducers 306. Consequently, the indifferent electrode 326 may be communicatively connected to the energy source device system 340 via one or more communication lines (not shown in FIG. 3A) in some embodiments. In addition, although shown separately in FIG. 3A, indifferent electrode 326 may be considered part of the energy source device system 340 in some embodiments. In some embodiments, the indifferent electrode 326 is provided outside the body (e.g., on a skin-based surface) or at least the bodily cavity in which the transducer-based device (e.g., 200, 300, or 400) or catheter system 500 is, at least in part, located.

In some embodiments, the energy source device system 340 may include one or more driving motors configured to drive movement, in response to instructions from the controller 324, of various actuators or other catheter system components to control deployment, expansion, retraction, or other manipulations of the shape, positioning, or both shape and positioning of the transducer-based device (e.g., manipulable portion) 300. In some embodiments, various manually operated or other catheter system components may be employed to control deployment, expansion, retraction, or other manipulations of the shape, positioning, or both shape and positioning of the transducer-based device (e.g., manipulable portion) 300. It is understood that input-output device system 320 may include other systems.

In some embodiments, input-output device system 320 may optionally include energy source device system 340, transducer-based device 300 or both energy source device system 340 and transducer-based device 300 by way of non-limiting example.

Structure 308 of transducer-based device 300 can be delivered and retrieved through a catheter member, for example, a catheter sheath 312. In some embodiments, the structure 308 provides expansion and contraction capabilities for a portion of a medical device (e.g., an arrangement, distribution or array of transducers 306). The transducers 306 can form part of, be positioned or located on, mounted or otherwise carried on the structure and the structure may be configurable to be appropriately sized to slide within a lumen of catheter sheath 312 in order to be deployed percutaneously or intravascularly. FIG. 3A shows one embodiment of such a structure. In some embodiments, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In various embodiments, the intermediate portion 309 of each of the elongate members 304 includes a respective pair of side edges of the front surface 318a, the back surface 318b, or both the front surface 318a and the back surface 318b, the side edges of each pair of side edges opposite to one another, the side edges of each pair of side edges extending between the proximal end 307 and the distal end 305 of the respective elongate member 304. In some embodiments, each pair of side edges includes a first side edge 327a (only one called out in FIG. 3A) and a second side edge 327b (only one called out in FIG. 3A). In some embodiments, each of the elongate members 304, including each respective intermediate portion 309, is arranged front surface 318a-toward-back surface 318b in a stacked array during an unexpanded or delivery configuration (e.g., FIG. 3A). In many cases, a stacked array allows the structure 308 to have a suitable size for percutaneous or intravascular delivery. A stacked array can allow structure 308 to have a spatially efficient size for delivery through a lumen of catheter sheath 312. In some embodiments, the elongate members 304 are arranged to be introduced into a bodily cavity distal end 305 first. For clarity, not all of the elongate members 304 of structure 308 are shown in FIG. 3A. A flexible catheter body or shaft 314 is used to deliver structure 308 through catheter sheath 312. In some embodiments, each elongate member includes a twisted portion proximate proximal end 307.

In some embodiments, the elongate members 304 are arranged in a fanned arrangement 370 in FIG. 3B, e.g., where they are angularly spaced with respect to one another about an axis. Such an axis, in some embodiments of FIG. 3B, may pass through opposite 'poles' of the fanned arrangement 370, like axis 375 shown, for example, as a broken line in FIG. 3B. However, other embodiments are not limited to any particular fanning axis. In some embodiments, the fanned arrangement 370 is formed during the expanded or deployed configuration in which the transducer-based device (e.g., manipulable portion) 300 or structure 308 thereof is manipulated to have a size, shape, or both size and shape too large for percutaneous or intravascular delivery, for example a size, shape, or both size and shape too large for percutaneous or intravascular delivery toward a bodily cavity, or a size, shape, or both size and shape too large for percutaneous or intravascular delivery away from a bodily cavity. In some embodiments, the fanned arrangement 370 is formed during the expanded or deployed configuration in which the transducer-based device (e.g., manipulable portion) 300 or structure 308 thereof is manipulated to have a size, shape, or both size and shape too large for delivery through a lumen of catheter sheath 312, for example, a size, shape, or both size and shape too large for delivery through a lumen of catheter sheath 312 toward a bodily cavity, or a size, shape, or both size and shape too large for delivery through a lumen of catheter sheath 312 away from a bodily cavity.

In some embodiments, the transducer-based device (e.g., manipulable portion) 300 or structure 308 thereof includes a proximal portion 308a having a first domed shape 309a and a distal portion 308b having a second domed shape 309b when the transducer-based device (e.g., manipulable portion) 300 or structure 308 thereof is in the expanded or deployed configuration. In some embodiments, the proximal and the distal portions 308a, 308b include respective portions of elongate members 304. In some embodiments, the transducer-based device (e.g., manipulable portion) 300 or structure 308 thereof is arranged to be delivered or advanced distal portion 308b first into a bodily cavity when the transducer-based device (e.g., manipulable portion) 300 or structure 308 thereof is in the unexpanded or delivery configuration as shown in FIG. 3A. In some embodiments, the proximal and the distal portions 308a, 308b are arranged in a clam shell configuration in the expanded or deployed configuration shown in FIG. 3B. In various example embodiments, each of the front surfaces 318a of the intermediate portions 309 of the plurality of elongate members 304 face outwardly from the structure 308 when the structure 308 is in the deployed configuration. In various example embodiments, each of the front surfaces 318a of the intermediate portions 309 of the plurality of elongate members 304 are positioned adjacent an interior tissue surface of a bodily cavity in which the structure 308 (i.e., in the deployed configuration) is located. In various example embodiments, each of the back surfaces 318b of the intermediate portions 309 of the plurality of elongate members 304 face an inward direction when the structure 308 is in the deployed configuration.

The transducers 306 may be arranged in various distributions or arrangements in various embodiments. In some embodiments, various ones of the transducers 306 are spaced apart from one another in a spaced apart distribution in the delivery configuration shown in FIG. 3A. In some embodiments, various ones of the transducers 306 are arranged in a spaced apart distribution in the deployed configuration shown in FIG. 3B. In some embodiments, various pairs of transducers 306 are spaced apart with respect to one another. In some embodiments, various regions of space are located between various pairs of the transducers 306. For example, in FIG. 3B the transducer-based device 300 includes at least a first transducer 306*a*, a second transducer 306*b* and a third transducer 306*c* (all collectively referred to as transducers 306). In some embodiments each of the first, the second, and the third transducers 306*a*, 306*b* and 306*c* are adjacent transducers in the spaced apart distribution. In some embodiments, the first and the second transducers 306*a*, 306*b* are located on different elongate members 304 while the second and the third transducers 306*b*, 306*c* are located on a same elongate member 304. In some embodiments, a first region of space 350 is between the first and the second transducers 306*a*, 306*b*. In some embodiments, the first region of space 350 is not associated with any physical portion of structure 308. In some embodiments, a second region of space 360 associated with a physical portion of device 300 (i.e., a portion of an elongate member 304) is between the second and the third transducers 306*b*, 306*c*. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter device. For example, an elongated catheter member may be used to distribute the transducers in a linear or curvilinear array. Basket catheters or balloon catheters may be used to distribute the transducers in a two-dimensional or three-dimensional array.

In some embodiments, a manipulable portion, such as, but not limited to, a transducer-based device (e.g., 200 or 300) is manipulated to transition between a delivery configuration (e.g., FIG. 3A) and an expanded or deployed configuration (e.g., FIG. 3B) manually (e.g., by a user's manual operation) or at least in part by way of motor-based driving (e.g., from the energy source device system 340) of one or more actuators or other catheter system components. Motor-based driving may augment or otherwise be in response to manual actions, may be responsive to automated control of a data processing device system (e.g., 110 in FIG. 1 or 310 in FIGS. 3A and 3B), or may use a hybrid manual-automated approach.

FIG. 5 illustrate mechanisms for, among other things, limiting spacing between elongate members (e.g., 304), according to some embodiments of the present invention. In this regard, FIG. 5 illustrate all or one or more portions of a medical system, according to various embodiments.

Figure 5A:
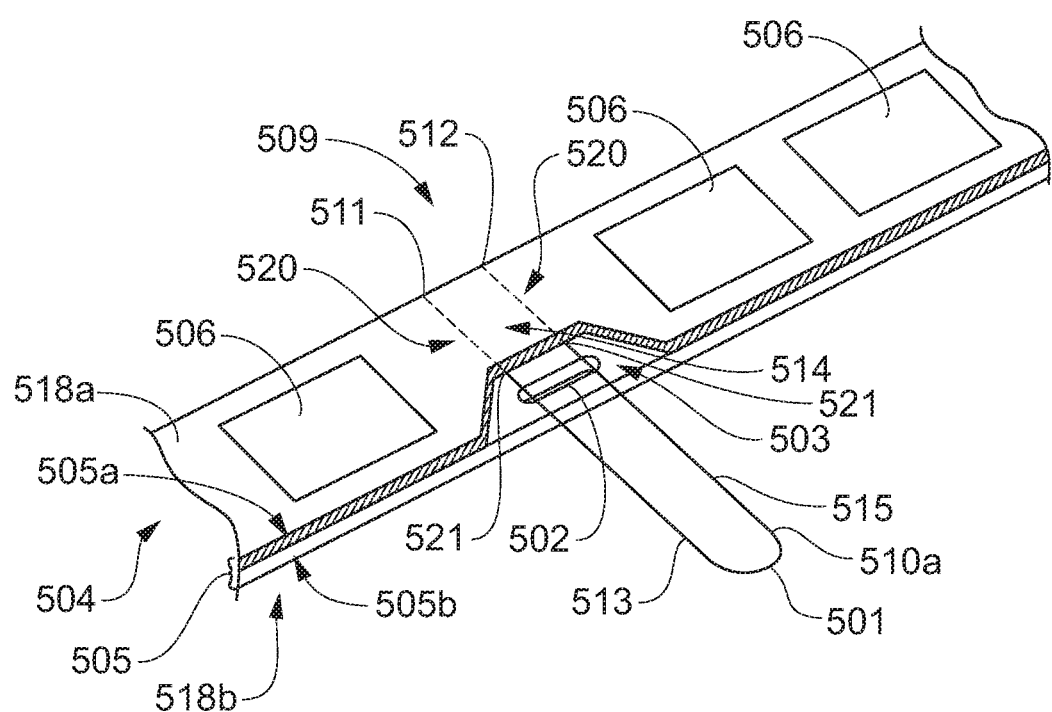

FIG. 5A illustrates an intermediate portion 509 of an elongate member 504, which may correspond to an intermediate portion 309 of an elongate member 304 in some embodiments. The elongate member 504 may include transducers 506, which may correspond to the transducers 220, 306, or 406. The elongate member 504 may include material layers 505, which may correspond to the layers 404 and 403. FIG. 5A shows only two material layers 505*a*, 505*b* for example purposes only, although, as shown in FIG. 4, more layers may be present. In some embodiments one material layer (e.g., 505*a*) may correspond to a flexible layer 403 from FIG. 4, an electrically conductive layer 404 from FIG. 4, or both a flexible layer 403 and an electrically conductive layer 404 from FIG. 4.

The elongate member 504 may include a first surface or side 518*a* and a second surface or side 518*b*, which may respectively correspond to the front surface 318*a* and rear surface 318*b*. In some embodiments, the elongate member 504 includes a notch 503 in at least one of the layers 505 (the notch 503 is shown in FIG. 5A through only one layer for example purposes only). Some instances of the notch 503 are called out in FIG. 3B, although more are present. In some embodiments, the notch 503 includes an aperture 502 which passes through the elongate member 504 from the first side 518*a* to the second side 518*b*. It should be noted that the shape of aperture 502 may take other forms than the pill shape shown in the figures, such as round, square, triangular, rectangular, or any other shape. In some embodiments, the aperture 502 extends across a thickness of the elongate member 504 from the first side 518*a* to the second side 518*b*. In this regard, the first side 518*a* may be considered to include the exposed top or front (e.g., tissue facing) surfaces of multiple ones of the layers 505, according to some embodiments. In the example of FIG. 5A, the first side 518*a* may be considered to include the exposed front (e.g., tissue facing) surface of the front-most layer 505*a* in addition to the exposed front (e.g., tissue facing) surface of the layer 505*b* underlying layer 505*a* where the notch 503 resides, such that the aperture 502 is considered to pass through the elongate member 504 from the first side 518*a* to the second side 518*b*.

In some embodiments, the elongate member 504 includes a flexible coupling 501, which may be a tie line, made from a material such as Dyneema (a Trademark of DSM IP Assets B.V. LIMITED LIABILITY COMPANY NETHERLANDS Het Overloon 1 NL-6411 TE HEERLEN NETHERLANDS) Purity. The tie line may have a braid specification: 4×25 dtex 25 PPI, for example as manufactured by Cortland Limited having a place of business at 44 River Street, Cortland, N.Y. 13045, USA. A few instances of the flexible coupling 501 are shown in FIG. 3B, although others may be present. The flexible coupling 501 may include portions 520 (shown in broken lines in FIG. 5A) located between adjacent material layers 505 (shown between a bottom layer 505*b* and top layer 505*a* in FIG. 5A for example purposes only, although in embodiments including more than two layers, the portions 520 may be located between at least two adjacent ones of those layers) in order to secure the flexible coupling 501 to the elongate member 504. In some embodiments, the portions 520 located between layers 505 may terminate at separate first and second ends, where the first end is represented with reference numeral 511, and the second end is represented with reference numeral 512. The portions 520 of the flexible coupling 501 located between layers 505 may be formed at such location as part of the process of manufacturing the elongate member 504, so that the portions 520 (or first and second ends 511, 512 in some embodiments) are physically coupled to the intermediate portion 509 of the elongate member 504, for example, by lamination, an adhering process, or other sealing process between adjacent material layers 505. The portions 520 of the flexible coupling 501 located between layers 505 may be formed at such location as part of the process of manufacturing the elongate member 504, so that the portions 520 (or first and second ends 511, 512 in some embodiments) are, for example, laminated, adhered, or otherwise sealed between a flexible circuit assembly layer and a support structure layer.

The flexible coupling 501 may exit from between layers 505 at points 521, lay across the aperture 502 (i.e., not pass through aperture 502 in some embodiments), and extend transversely from the intermediate portion 509 of the elongate member 504, the flexible coupling 501 extending with an elongated portion 513 to form at least a portion of a part 515 of a closed loop 510a that follows a continuous closed path. In some embodiments, another part (or the rest) 514 of the closed loop 510a is formed by the elongate member 504. In some embodiments, the part 514 may be an elongate portion of the elongate member 504 extending between a first end portion (e.g., 511 or 520) and a second end portion (e.g., 512 or the other 520) of the flexible coupling 501. In some embodiments, the first end portion, the second end portion, or both includes a respective terminating end of the flexible coupling 501. In some embodiments, the first end portion, the second end portion, or both does not include a respective terminating end of the flexible coupling 501. In some embodiments, the part 514 may be at least part of the intermediate portion 509 of the elongate member 504 between the layers 505 and between the portions 520, such part 514 being laminated, adhered, or otherwise sealed together to close the loop 510a or the continuous closed path thereof, according to some embodiments. In some embodiments, the part 514 of the closed loop 510a is formed by the flexible coupling itself, for example, in some embodiments where the portions 511, 512 of the flexible coupling 501 are connected to each other so that the entire flexible coupling 501 is a closed loop, instead of having portions 511, 512 separated as shown in FIG. 5A.

Figure 5B:
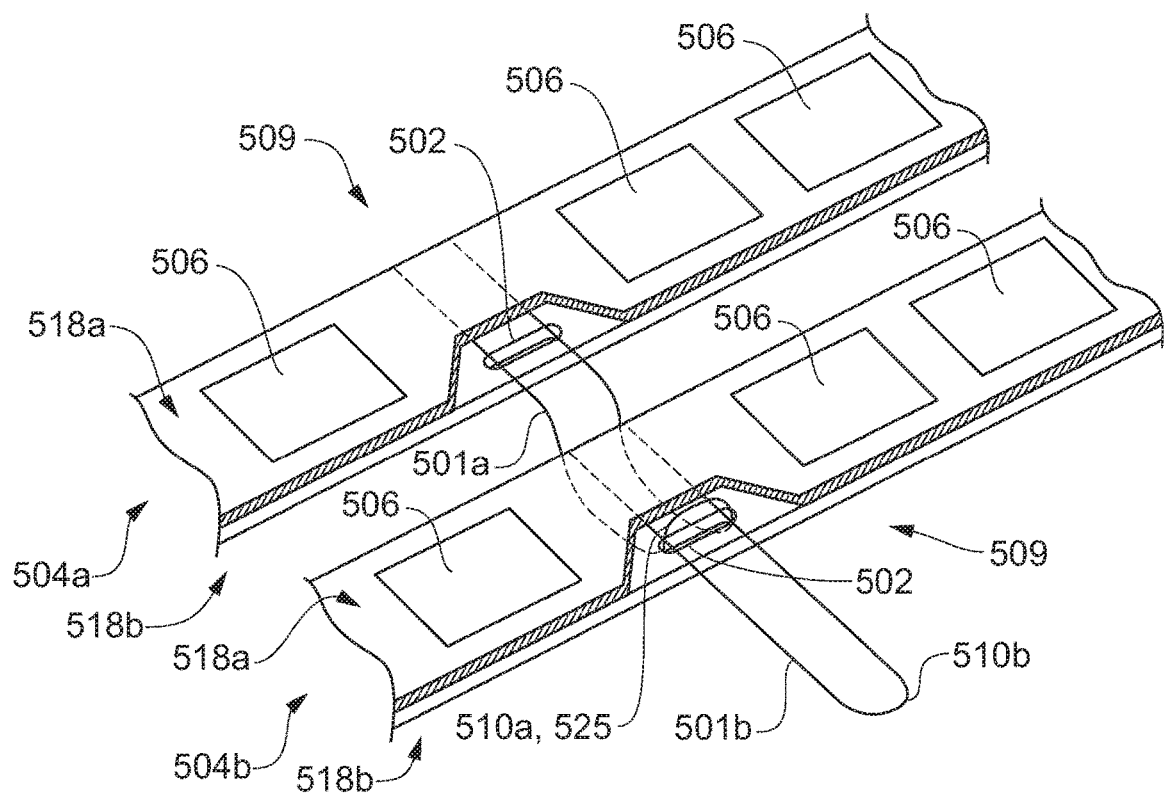

FIG. 5B illustrates a connection between a first elongate member 504a and a second elongate member 504b, each of which represents an instance of elongate member 504. In this regard, each of a first flexible coupling 501a of the first elongate member 504a and a second flexible coupling 501b of the second elongate member 504b represents an instance of flexible coupling 501 (flexible coupling 501 is shown in FIG. 5A). Collectively, elongate members 504a, 504b may represent two adjacent elongate members 304.

Figure 5C:
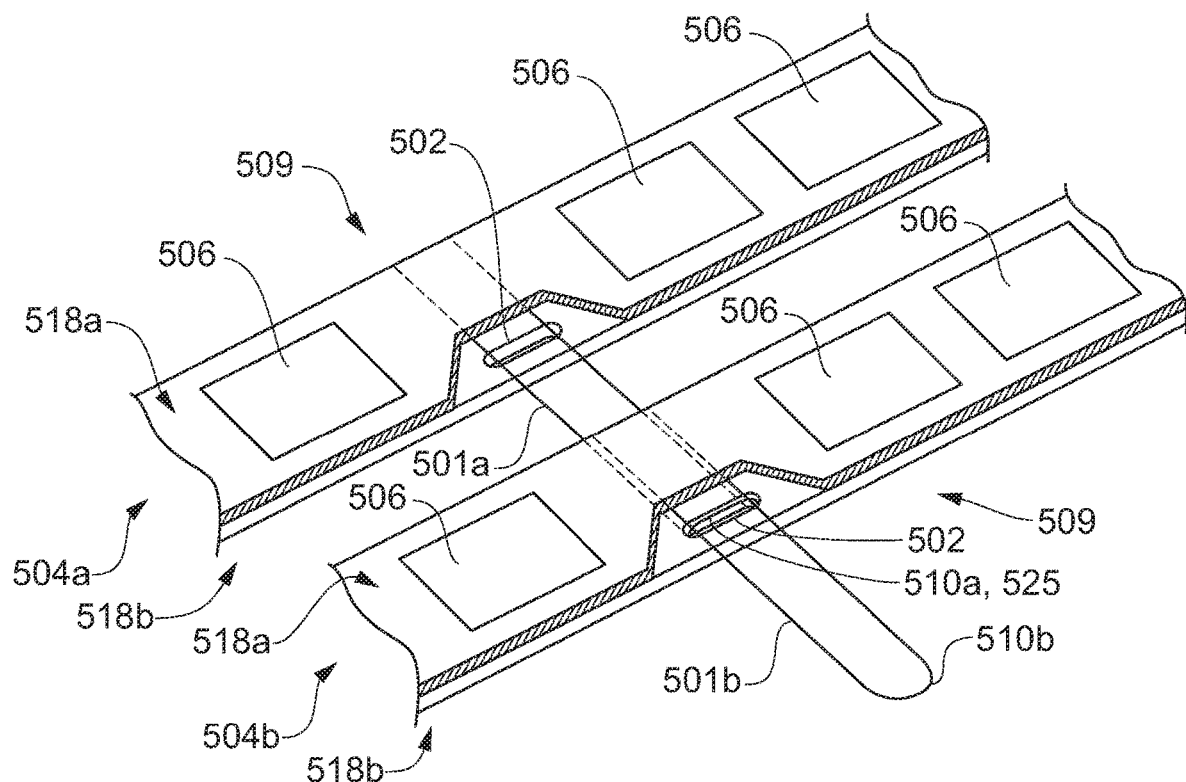

In FIG. 5B, first flexible coupling 501a extends under (i.e., along the second side 518b of) the second elongate member 504b and then up and through the aperture 502 (i.e., from the second side 518b to the first side 518a) of the second elongate member 504b, thereby creating a loop 525 at an end of the first flexible coupling 501a through which the second flexible coupling 501b is received and passes. (Note that the broken lines in FIG. 5 represent either the passing of a flexible coupling 501 under an elongate member or between layers 505 of an elongate member.) As shown in FIG. 5C, this looping arrangement with loop 525 limits a spacing between the elongate members 504a and 504b (e.g., at least the intermediate portions 509 thereof) so as not to exceed a defined amount (e.g., when the structure 308 or a similar structure comprising elongate members 504 is in its expanded or deployed configuration or when the first flexible coupling 501a is in a tension state).

In some embodiments, the first closed loop 510a extends along a path from the intermediate portion 509 of the first elongate member 504a through the aperture 502 (i.e., from the second side 518b to the first side 518a of the intermediate portion) of the second elongate member 504b to a location where a portion of the flexible coupling 501b of the second elongate member 504b is arranged to extend or pass through the first closed loop 510a (e.g., loop 525).

In some embodiments, the aperture 502 of at least the second elongate member 504b is sized to restrict movement of the first closed loop 510a through the aperture 502 from the first side 518a toward the second side 518b of the intermediate portion 509 of the second elongate member 504b when a portion of the flexible coupling 501b of the second elongate member 504b extends or passes through the first closed loop 510a. For example, as shown in FIGS. 5B and 5C, the loop 525 is restricted from returning from the first side 518a toward the second side 518b of the intermediate portion 509 of the second elongate member 504b through the aperture 502 of the second elongate member 504b. For another example, in some embodiments, the aperture 502 has a size sufficient to allow two portions or segments of a flexible coupling (e.g., two opposing portions of loop 525 of flexible coupling 501a fitting through aperture 502) to fit within it, but insufficient to allow four portions or segments of a flexible coupling (e.g., two portions or segments of flexible coupling 501b) to fit within it. (Note that the thickness of the flexible couplings (e.g., 501, 501a, 501b) illustrated in the figures, the size of the aperture 502 illustrated in the figures, or both, may be different than that shown, as the illustrated dimensions are for purposes of illustrating aspects of some embodiments.) In this regard, in some embodiments, when the flexible coupling 501b of the second elongate member 504b extends through loop 525, the loop 525 may be prevented from returning through the aperture 502 of the second elongate member 504b not only by the flexible coupling 501b extending through it, but also by a limited size of the aperture 502, which may be sized to prevent both flexible couplings 501a and 501b from passing therethrough.

In FIGS. 5B and 5C, the flexible coupling 501b extending transversely from the intermediate portion 509 of the second elongate member 504b may form at least part of a second closed loop 510b, according to some embodiments. In this regard, as shown in FIG. 5C, in some embodiments, no portion of the flexible coupling 501a extending transversely from the intermediate portion 509 of the first elongate member 504a is received through the second loop 510b at least when the spacing between the respective locations of the first and second elongate members 504a, 504b is sized by a defined amount. In some embodiments, according to FIG. 5C, no portion of the flexible coupling 501a extending transversely from the intermediate portion 509 of the first elongate member 504a is received through the second loop 510b when the flexible coupling 501a extending transversely from the intermediate portion 509 of the first elongate member 504a is tensioned. In some embodiments according to FIGS. 5B and 5C, each of the first and the second closed loops 510a, 510b extends along a respective continuous closed path, each respective continuous closed path not encircling the other respective continuous closed path. For example, in some embodiments according to FIGS. 5B and 5C, at least a portion of the flexible coupling 501a exists outside of the continuous closed path of the flexible coupling 501b, and vice versa. In some embodiments according to FIGS. 5B and 5C, the continuous closed path of the first closed loop 510a does not pass through the continuous closed path of the second closed loop 510b (for example, at least when (a) the flexible coupling 501a extending transversely from the intermediate portion 509 of the first elongate member 504a is tensioned; (b) the flexible coupling 501b extending transversely from the intermediate portion 509 of the second elongate member 504b is tensioned; or both (a) and (b)). In some embodiments according to FIGS. 5B and 5C, the continuous closed path of the second closed loop 510*b* does pass through the continuous closed path of the first closed loop 510*a* (for example, at least when (a) the flexible coupling 501*a* extending transversely from the intermediate portion 509 of the first elongate member 504*a* is tensioned; (b) the flexible coupling 501*b* extending transversely from the intermediate portion 509 of the second elongate member 504*b* is tensioned; or both (a) and (b)). In some embodiments, as shown in FIGS. 5B and 5C, the first closed loop 510*a* surrounds a portion of the second closed loop 510*b* at loop 525, but not vice versa, at least when (a) the flexible coupling 501*a* extending transversely from the intermediate portion 509 of the first elongate member 504*a* is tensioned; (b) the flexible coupling 501*b* extending transversely from the intermediate portion 509 of the second elongate member 504*b* is tensioned; or both (a) and (b)). In other words, in some embodiments, only one flexible coupling (e.g., 501*a*) in a pair of adjacent flexible couplings (e.g., 501*a*, 501*b*) surrounds the other flexible coupling (e.g., 501*b*) in the pair of adjacent flexible couplings. Stated differently, in some embodiments, only one flexible coupling (e.g., 501*b*) in a pair of adjacent flexible couplings (e.g., 501*a*, 501*b*) passes through the other flexible coupling (e.g., 501*a*) in the pair of adjacent flexible couplings. In other words, in some embodiments, the flexible couplings in a pair of adjacent flexible couplings (e.g., 501*a*, 501*b*) do not (a) surround a portion of each other, (b) pass through each other, or both (a) and (b). In this regard, in some embodiments, the second closed loop 510*b* does not extend along a closed continuous path that completely surrounds any portion of the first closed loop 510*a* at least in a state where the first closed loop 510*a* extends along a closed continuous path that completely surrounds any portion of the second closed loop 501*b*, or vice versa, at least when (a) the flexible coupling 501*a* extending transversely from the intermediate portion 509 of the first elongate member 504*a* is tensioned; (b) the flexible coupling 501*b* extending transversely from the intermediate portion 509 of the second elongate member 504*b* is tensioned; or both (a) and (b)). Stated differently, in some embodiments, the first closed loop 510*a* does not pass through any portion of the second closed loop 510*b* in a state where the second closed loop 510*b* passes through any portion of the first closed loop 510*a*, or vice versa, at least when (a) the flexible coupling 501*a* extending transversely from the intermediate portion 509 of the first elongate member 504*a* is tensioned; (b) the flexible coupling 501*b* extending transversely from the intermediate portion 509 of the second elongate member 504*b* is tensioned; or both (a) and (b)).

Figure 5D:
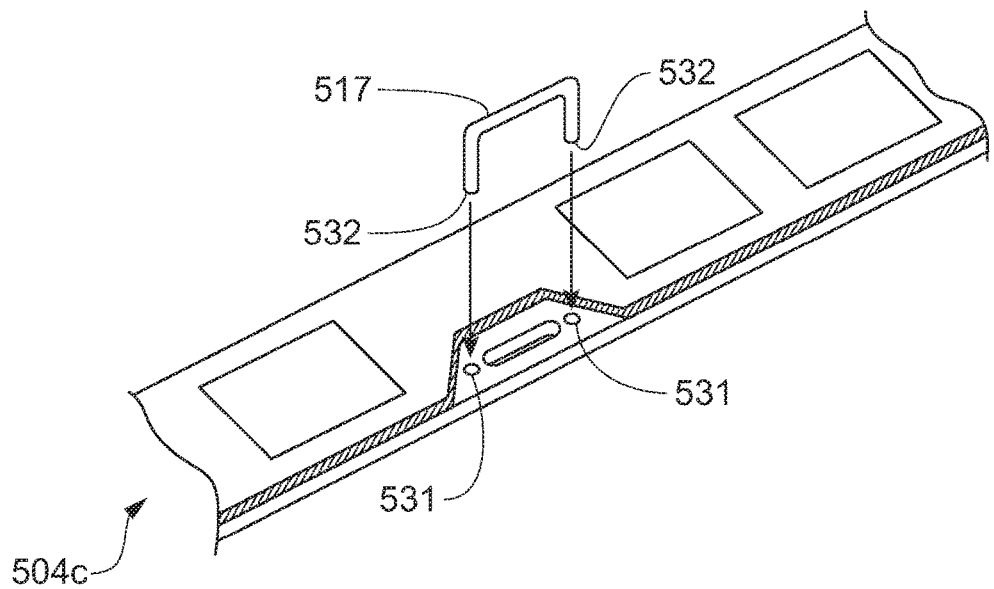
Figure 5E:
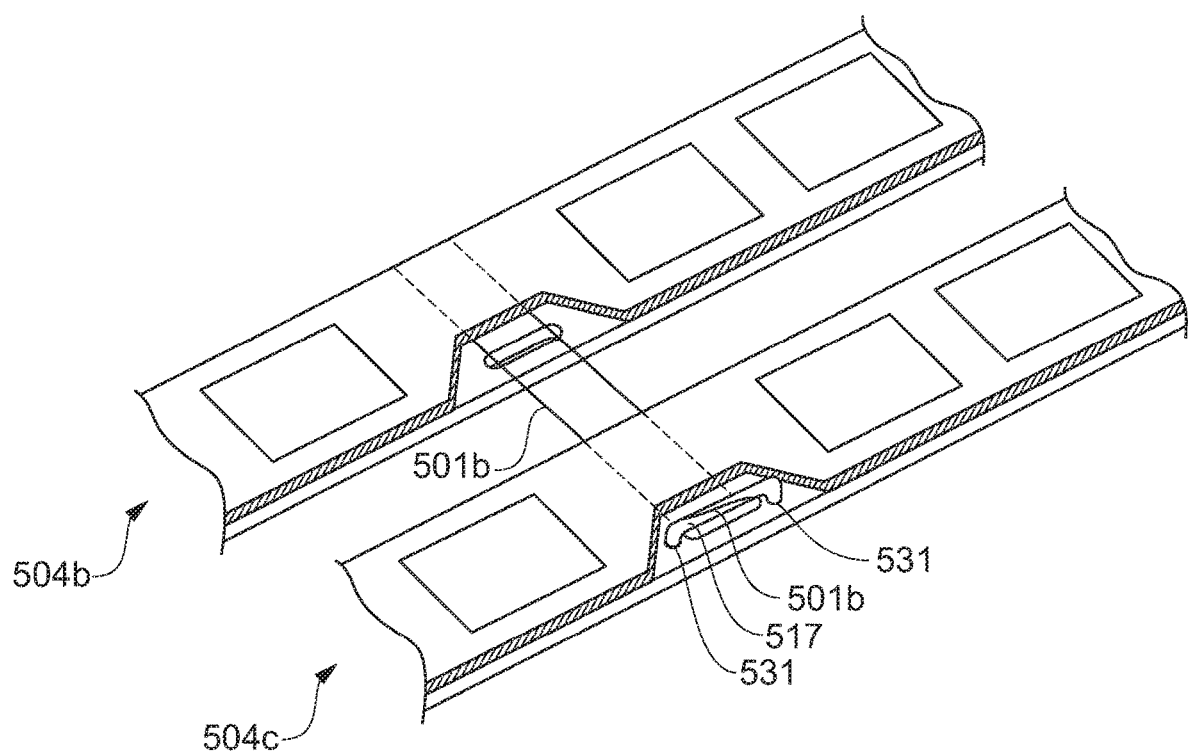
Figure 5F:
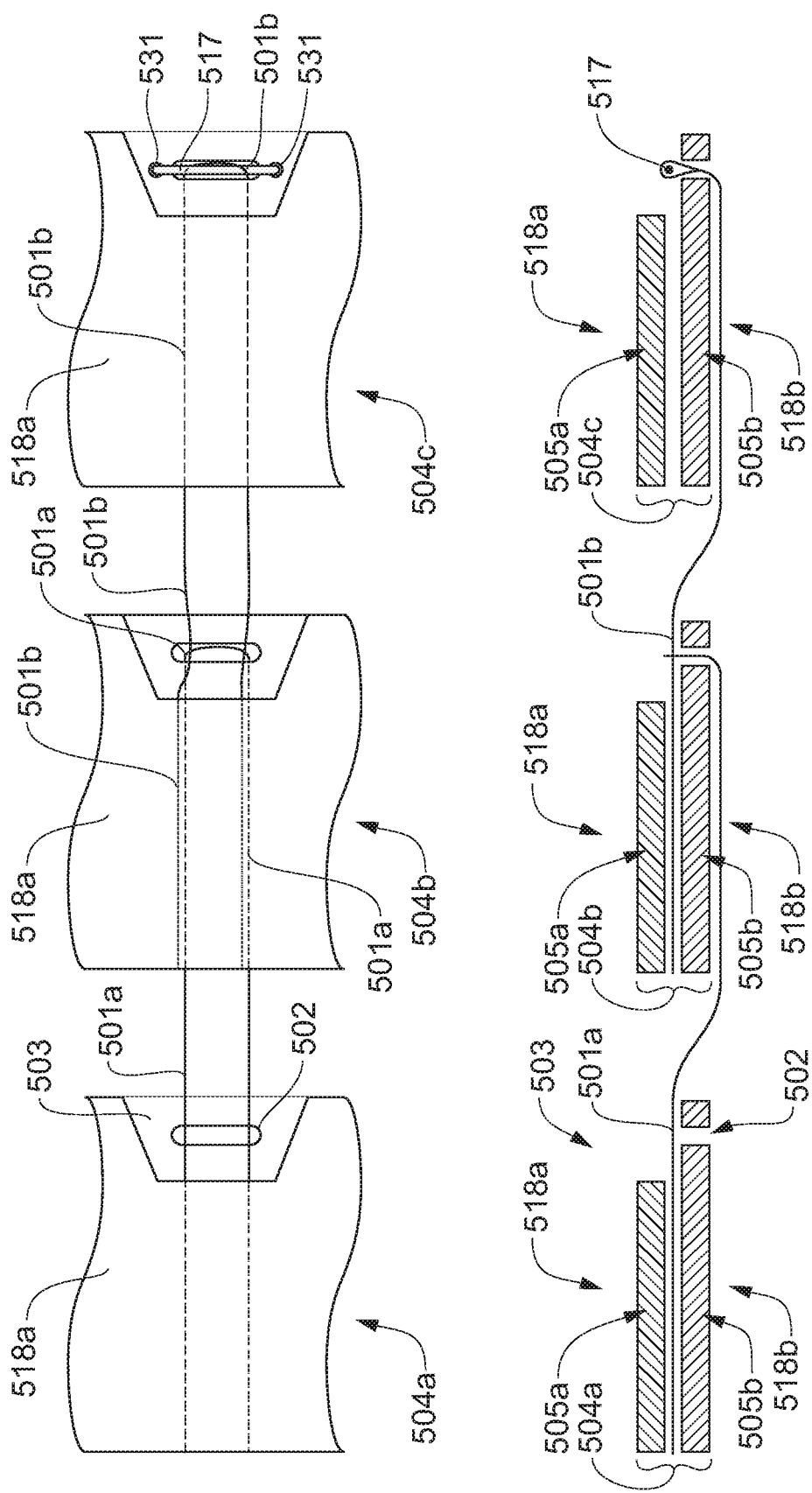

FIG. 5D illustrates a securing mechanism 517, such as a staple or other fastening device, that may be used to terminate the daisy-chaining structure illustrated in FIGS. 5B and 5C. In some embodiments, respective openings 531 that pass through at least a portion of the elongate member 504 (e.g., notch 503, one or more layers 505, such as bottom layer 505*b* shown in FIG. 5A) are configured to receive respective ends 532 of the securing mechanism 517. As shown in FIG. 5E, the flexible coupling 501*b* of the second elongate member 504*b* may be terminated at a third elongate member 504*c* (which may be an instance of elongate members 504) by being tied to, or looped around, the securing mechanism 517. In this regard, FIG. 5F illustrates plan and side views of the elongate members 504*a*, 504*b*, and 504*c*, according to some embodiments. FIG. 3B also illustrates an instance of the securing mechanism 517, according to some embodiments. In various embodiments in which securing mechanism 517 includes a staple-like form, various ones of the legs of the staple-like form may be secured to the elongate member 504 by various techniques including welding, adhesive bonding, or a combination thereof.

FIGS. 5G, 5H-1, and 5H-2 illustrate some embodiments where a flexible coupling 501 connecting adjacent elongate members 504 is itself formed as a closed loop. For example, FIGS. 5G, 5H-1, and 5H-2 illustrate some embodiments where separated portions 511, 512 shown, for example, in FIG. 5A are connected, not separated. In this regard, the flexible coupling may be caused to form such a closed loop by knotting, adhering, fusing, or otherwise connecting the ends of such flexible coupling.

While FIGS. 5G, 5H-1, and 5H-2 illustrate some embodiments where the flexible couplings 501 are connected to elongate members 504 via apertures 502 without any portion of the flexible couplings 501 located between material layers 505 of an elongate member 504, it should be noted that other embodiments may locate one or more portions of a flexible coupling 501 between material layers 505 at least as discussed above with respect to FIGS. 5A-5F.

Figure 5G:
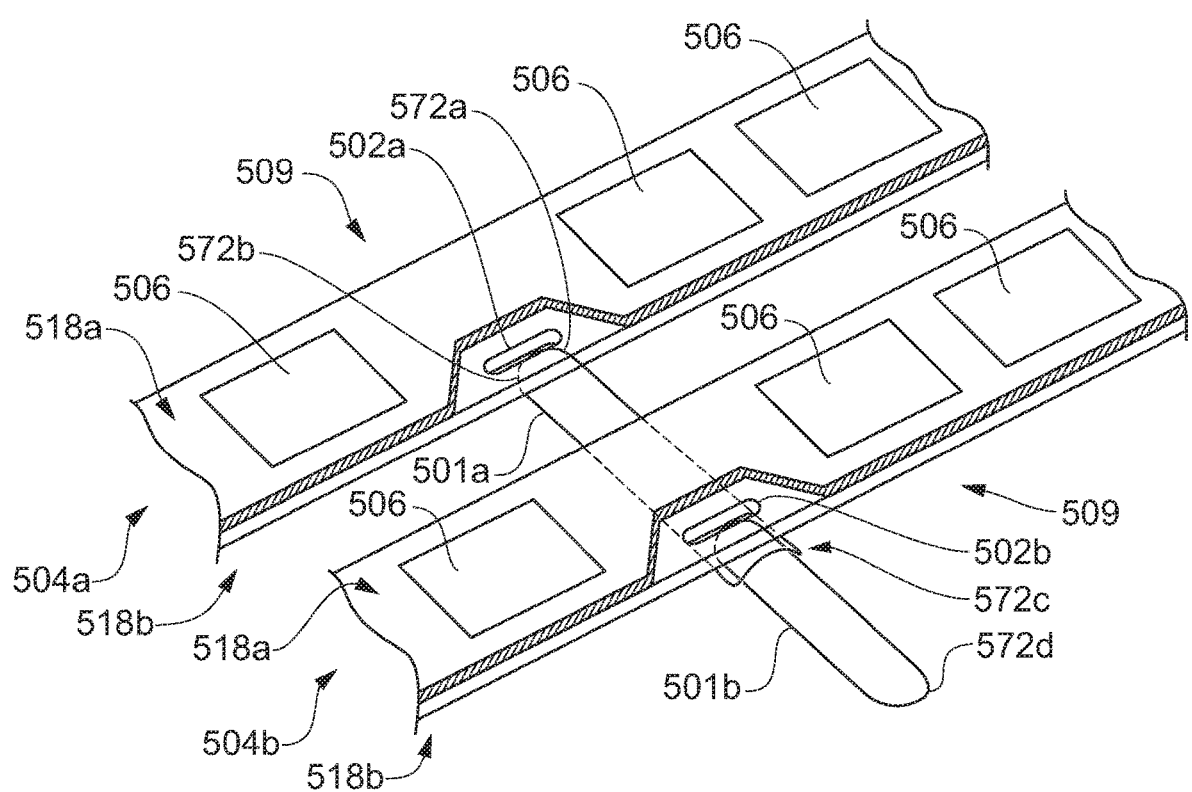

In some embodiments according to FIG. 5G, the flexible coupling 501*a* is arranged as a closed loop that passes through the aperture 502*a* of the elongate member 504*a* with one portion 572*a* of the flexible coupling 501*a* exiting the aperture 502*a* in a direction heading above the first (e.g., front) surface 518*a* of the elongate member 504*a*, and another portion 572*b* of the flexible coupling 501*a* exiting the aperture 502*a* in a direction heading underneath the second (e.g., rear) surface 518*b* of the elongate member 504*a*. The flexible coupling 501*a* may then extend underneath the adjacent elongate member 504*b* (e.g., as shown by the corresponding broken line in FIG. 5G) to a location 572*c* where the flexible couplings 501*a* and 501*b* link to each other, according to some embodiments. For example, flexible coupling 501*b* may pass through the closed loop of flexible coupling 501*a* at location 572*c* according to some embodiments. In some embodiments, flexible coupling 501*b* is connected to elongate member 504*b* via aperture 502*b* in a manner that is similar to, or the same as, that employed to couple flexible coupling 501*a* to elongate member 501*a* in FIG. 5G. The flexible coupling 501*b* may then extend toward a next elongate member (not shown) adjacent elongate member 504*b*, in some embodiments. In this regard, portion 572*d* of flexible coupling 501*b* may link to a flexible coupling (not shown) of the next elongate member (not shown) in a similar or same manner as flexible coupling 501*a* is linked to flexible coupling 501*b* in FIG. 5G. Accordingly, this process of connecting adjacent elongate members according to FIG. 5G may be repeated to connect many elongate members, just as the processes of the other FIG. 5 may be repeated (e.g., repeating FIG. 5C to a termination point as shown in FIG. 5F) to connect many elongate members. Also as with the other FIG. 5 (e.g., FIGS. 5D-5F), the connection process of FIG. 5G may terminate at a securing mechanism 517, according to some embodiments. It is noted that in some embodiments, at least part of flexible coupling 501*a* of FIG. 5G may extend through aperture 502*b* of adjacent elongate member 504*b*. For example, flexible coupling 501*a* may extend through aperture 502*b* of adjacent elongate member 504*b* and terminate at a securing mechanism (e.g., 517), according to some embodiments.

Figures 1, 5H:
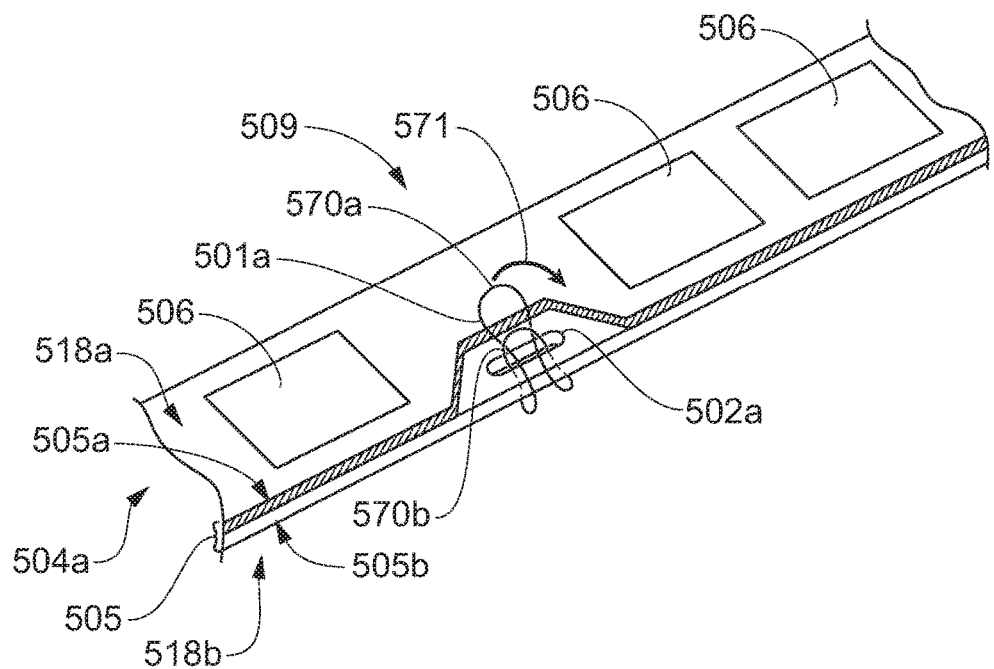
Figures 2, 5H:
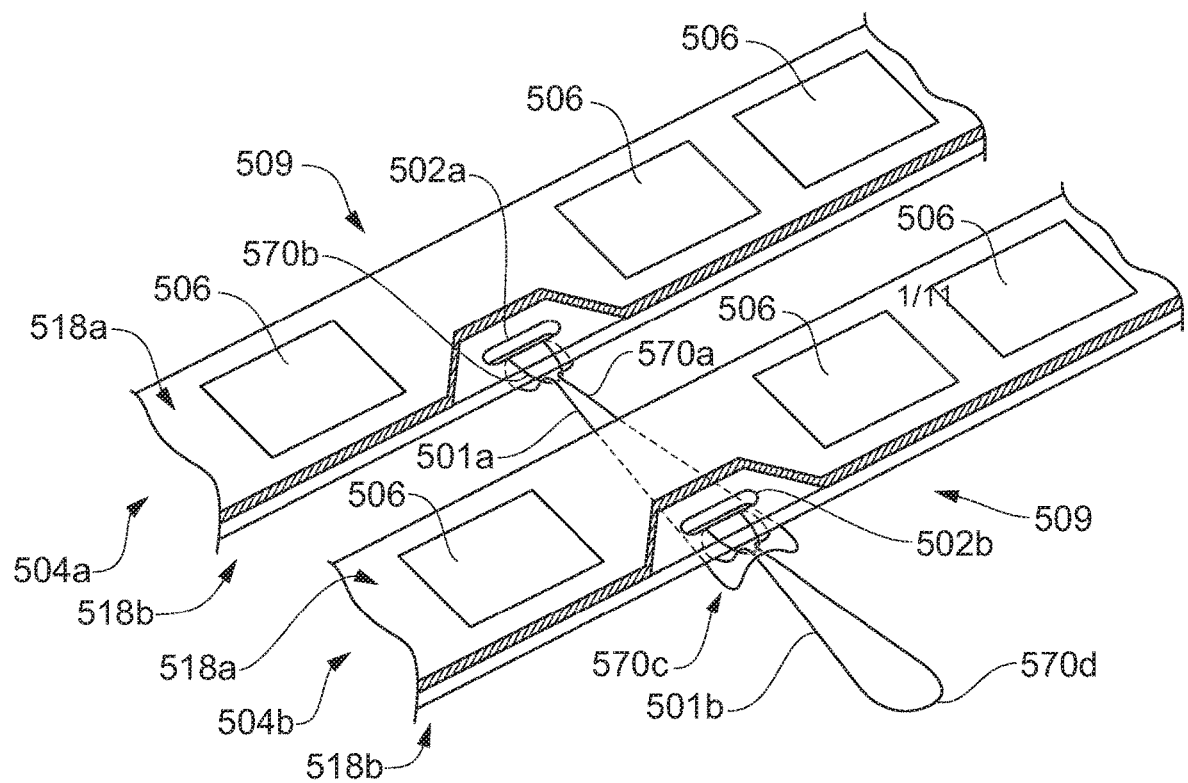

FIGS. 5H-1 and 5H-2 illustrate some other embodiments in which at least flexible coupling 501*a* is formed as a closed loop. FIG. 5H-1 illustrates the flexible coupling 501*a* in an intermediate, loose, state where it is not connected to an adjacent elongate member, according to some embodiments.

FIG. 5H-2 illustrates the flexible coupling 501a of FIG. 5H-1 in a tensioned state where such flexible coupling 501a is connected or coupled to adjacent elongate member 504b, according to some embodiments. As shown in FIG. 5H-1, according to some embodiments, the flexible coupling 501a includes a first loop portion 570a that passes through a second loop portion 570b of the flexible coupling 501a. The second loop portion 570b has passed up through aperture 502a from the second (e.g., rear) side 518b to the first (e.g., front) side 518a of the elongate member 504a when the first loop portion 570a passes through the second loop portion 570b, according to some embodiments. After passing through the second loop portion 570b, according to some embodiments, the first loop portion 570a is then pulled over the second loop portion 570b in the direction of the arrow 571 towards an adjacent elongate member (e.g., 504b) as shown in FIG. 5H-2. In this regard, in some embodiments, the first loop portion 570a may pass underneath the adjacent elongate member (e.g., 504b), as shown by the corresponding broken lines of portion 570a in FIG. 5H-2, and loop around the flexible coupling (e.g., 501b) of the adjacent elongate member (e.g., 504b) at location 570c, according to some embodiments. With reference to FIG. 5H-2, flexible coupling 501b may be connected to elongate member 504b in the same or similar manner that flexible coupling 501a is coupled to elongate member 504a. The flexible coupling 501b may extend toward a next elongate member (not shown) adjacent elongate member 504b, in some embodiments. In this regard, portion 570d of flexible coupling 501b may link to a flexible coupling (not shown) of the next elongate member (not shown) in the same or similar manner as flexible coupling 501a is linked to flexible coupling 501b. Accordingly, this process of connecting adjacent elongate members according to FIGS. 5H-1 and 5H-2 may be repeated to connect many elongate members, just as the processes of the other FIG. 5 may be repeated (e.g., repeating FIG. 5C to a termination point as shown in FIG. 5F) to connect many elongate members. Also as with the other FIG. 5 (e.g., FIGS. 5D-5F), the connection process of FIGS. 5H-1 and 5H-2 may terminate at a securing mechanism (e.g., 517), according to some embodiments.

As will be appreciated by a person of ordinary skill in the art, it is noted that the illustrations of flexible couplings 501 shown in various ones of FIGS. 3B and 5 may include distortions for clarity, such as the thickness, cross-sectional shape or size, or the manner and degree of bending, propagation, or linking of one or more flexible couplings 501. For one example, the illustration of the linking of flexible couplings 501a and 501b in FIG. 5H-2 is shown in a looser state than may be present in practice in order to more clearly show an example of how such flexible couplings 501a and 501b may be linked. Corresponding comments apply to at least FIG. 5G. Accordingly, some embodiments are not limited to the particular thickness, cross-sectional shape or size, or the manner and degree of bending, propagation, or linking of one or more flexible couplings 501 illustrated in the figures.

Advantageously, couplings such as couplings 501a and 501b can be easily formed with a desired tensioned length that allows a spacing between adjacent elongate members 504 to be maintained at a predetermined or defined amount in the expanded or deployed configuration. For example, a coupling such as coupling 501a or 501b may be accurately made by looping a tie line around an offset fixture pin and sandwiching the loose ends of the tie line between various layers that form the elongate member (e.g., as described above). Advantageously, flexible couplings such as couplings 501a and 501b greatly facilitate the assembly of the elongate members into the final structure (e.g., structure 308), at least because continuous long lengths of tie line that connect many elongate members need not be employed. In this regard, each of the flexible couplings (e.g., 510) of some embodiments may be relatively shorter than some conventional applications which use a long tie line to connect many elongate members, as each flexible coupling according to some embodiments, need only connect to the adjacent elongate member (e.g., 504). Multiple shorter distinct flexible couplings, e.g., 501 as according to some embodiments of the present invention, can be easier to manufacture than a single longer flexible coupling since couplings between the elongate members may be concurrently made as the elongate members are assembled into the final structure (e.g., structure 308) rather than after the elongate members are assembled into the final structure.

While some of the embodiments disclosed above are described with respect to an intra-cardiac cavity, the same or similar embodiments may be used for other bodily cavities, for example, gastric, bladder, arterial, or any lumen or cavity into which the devices according to any embodiment of the present invention may be introduced.

While some of the embodiments discussed above illustrate a particular number of elongate members that may be daisy-chained using respective flexible couplings 501, it should be noted that the invention is not limited to any particular number of elongate members that may be connected. In addition, while some embodiments discussed above illustrate a particular number of connection points (e.g., apertures 502) per elongate member by which the elongate member may be connected to one or more other elongate members, it should be noted that the invention is not limited to any particular number of such connection points per elongate member.

While the embodiments discussed above illustrate the connection of elongate members comprising transducers, the present invention is not limited to this configuration and may be applied to any expandable manipulable portion of an intra-cavity device that includes at least two elongate members.

While the embodiments discussed above illustrate the connection of elongate members along an equatorial intermediate region, the present invention is not limited to connecting elongate members in this region, and other regions may be used to connect the elongate members.

Subsets or combinations of various embodiments described above can provide further embodiments.

These and other changes can be made to the invention in light of the above-detailed description. In general, the terms used herein should not be construed to limit the invention to the specific embodiments disclosed in the specification, but should be construed to include other medical device systems including all medical treatment device systems and medical diagnostic device systems. Accordingly, the invention is not limited by the disclosure.

What is claimed is:

1. A medical system comprising:
   a shaft member including a portion sized to be delivered through a bodily opening leading to a bodily cavity; and
   a structure physically coupled to the shaft member, the structure including a plurality of elongate members, the structure selectively moveable between a delivery configuration in which the structure is suitably sized to be deliverable through the bodily opening to the bodily cavity, and an expanded configuration in which the structure has a size too large to be deliverable through the bodily opening to the bodily cavity, wherein each of at least one elongate member of the plurality of elongate members comprises a respective plurality of material layers, wherein a first subset of the respective plurality of material layers of the one elongate member contacts a second subset of the respective plurality of material layers of the one elongate member, an external surface of the first subset of the respective plurality of material layers of the one elongate member forming part of a first surface of the one elongate member, an external surface of the second subset of the respective plurality of material layers of the one elongate member forming at least part of a second surface of the one elongate member, and the first surface of the one elongate member and the second surface of the one elongate member forming opposing surfaces on opposite sides of the one elongate member, wherein the first subset of the respective plurality of material layers of the one elongate member includes a notch that exposes a surface of the second subset of the respective plurality of material layers of the one elongate member, the surface of the second subset of the respective plurality of material layers of the one elongate member that is exposed by the notch forming a portion of the first surface of the one elongate member, wherein the one elongate member comprises a plurality of transducers, and wherein the notch is located in a region of space between two adjacent transducers of the plurality of transducers, the two adjacent transducers adjacent along the one elongate member, and the region of space not including any transducer.

2. The medical system of claim 1,
wherein each elongate member of the plurality of elongate members comprises a proximal end, a distal end, and a respective intermediate portion positioned between the proximal end and the distal end, and wherein the notch is located within the respective intermediate portion of the one elongate member.

3. The medical system of claim 1, wherein the notch extends from an edge of the one elongate member, the edge between the first and second surfaces of the one elongate member.

4. The medical system of claim 1, wherein the notch has a trapezoidal shape.

5. The medical system of claim 1, wherein an aperture is formed at least in part in the surface of the second subset of the respective plurality of material layers of the one elongate member that is exposed by the notch.

6. The medical system of claim 5, wherein the surface of the second subset of the respective plurality of material layers of the one elongate member that is exposed by the notch surrounds the aperture.

7. The medical system of claim 1, wherein the first subset of the respective plurality of material layers of the one elongate member comprises an electrically conductive layer of a flexible circuit structure, and the second subset of the respective plurality of material layers of the one elongate member comprises a metallic structural layer.

8. The medical system of claim 1,
wherein the two adjacent transducers are a first transducer and a second transducer, and wherein the two adjacent transducers have a spacing therebetween along the one elongate member that is different than a spacing along the one elongate member between the first transducer and a third transducer of the plurality of transducers, the third transducer adjacent the first transducer along the one elongate member, and the third transducer other than the second transducer.

9. The medical system of claim 1,
wherein the notch is a first notch,
wherein a second elongate member of the plurality of elongate members is adjacent the one elongate member in the structure, at least in a state in which the structure is in the expanded configuration, and wherein the second elongate member includes a second notch in a location corresponding to a location of the first notch included in the first subset of the respective plurality of material layers of the one elongate member.

10. The medical system of claim 9, wherein the first notch and the second notch have corresponding sizes and shapes.

11. The medical system of claim 9, wherein the first notch and the second notch respectively extend from corresponding edges of the one elongate member and the second elongate member.

12. The medical system of claim 9,
wherein the second elongate member comprises a respective plurality of material layers, wherein a first subset of the respective plurality of material layers of the second elongate member contacts a second subset of the respective plurality of material layers of the second elongate member, an external surface of the first subset of the respective plurality of material layers of the second elongate member forming part of a first surface of the second elongate member, an external surface of the second subset of the respective plurality of material layers of the second elongate member forming at least part of a second surface of the second elongate member, and the first surface of the second elongate member and the second surface of the second elongate member forming opposing surfaces on opposite sides of the second elongate member, and wherein the first subset of the respective plurality of material layers of the second elongate member includes the second notch of the second elongate member, the second notch of the second elongate member exposing a surface of the second subset of the respective plurality of material layers of the second elongate member, the surface of the second subset of the respective plurality of material layers of the second elongate member that is exposed by the second notch of the second elongate member forming a portion of the first surface of the second elongate member.

13. The medical system of claim 12,
wherein a first aperture interrupts the surface of the second subset of the respective plurality of material layers of the one elongate member that is exposed by the first notch, and wherein a second aperture interrupts the surface of the second subset of the respective plurality of material layers of the second elongate member that is exposed by the second notch.

14. The medical system of claim 13, wherein the first aperture and the second aperture have corresponding locations along the one elongate member and the second elongate member, respectively.

15. The medical system of claim 14, wherein the first aperture and the second aperture have corresponding sizes and shapes.

16. The medical system of claim 13,
wherein the first aperture interrupts a region of the second surface of the one elongate member opposing the surface of the second subset of the respective plurality of material layers of the one elongate member that is exposed by the first notch, and
wherein the second aperture interrupts a region of the second surface of the second elongate member opposing the surface of the second subset of the respective plurality of material layers of the second elongate member that is exposed by the second notch.

17. The medical system of claim 13,
wherein the surface of the second subset of the respective plurality of material layers of the one elongate member that is exposed by the first notch surrounds the first aperture, and
wherein the surface of the second subset of the respective plurality of material layers of the second elongate member that is exposed by the second notch surrounds the second aperture.

18. The medical system of claim 12,
wherein a first aperture interrupts the external surface of the second subset of the respective plurality of material layers of the one elongate member,
wherein the first aperture extends from the external surface of the second subset of the respective plurality of material layers of the one elongate member to the surface of the second subset of the respective plurality of material layers of the one elongate member that is exposed by the first notch,
wherein a second aperture interrupts the external surface of the second subset of the respective plurality of material layers of the second elongate member, and
wherein the second aperture extends from the external surface of the second subset of the respective plurality of material layers of the second elongate member to the surface of the second subset of the respective plurality of material layers of the second elongate member that is exposed by the second notch.

19. The medical system of claim 12,
wherein a first aperture extends from the first surface of the one elongate member to the second surface of the one elongate member, and
wherein a second aperture extends from the first surface of the second elongate member to the second surface of the second elongate member.

20. The medical system of claim 1,
wherein each elongate member of the plurality of elongate members comprises a proximal end, a distal end, and a respective intermediate portion positioned between the proximal end and the distal end, and
wherein the respective intermediate portions of at least two elongate members of the plurality of elongate members are angularly spaced with respect to one another about an axis when the structure is in the expanded configuration.

21. The medical system of claim 20, wherein the at least two elongate members of the plurality of elongate members include the one elongate member.

* * * * *